(12) United States Patent
Nakayama et al.

(10) Patent No.: US 10,604,503 B2
(45) Date of Patent: Mar. 31, 2020

(54) CURABLE COMPOSITION, CURED PRODUCT, OPTICAL MEMBER, LENS, AND COMPOUND

(71) Applicant: FUJIFILM Corporation, Tokyo (JP)

(72) Inventors: Takafumi Nakayama, Ashigarakami-gun (JP); Naoyuki Morooka, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 16/266,778

(22) Filed: Feb. 4, 2019

(65) Prior Publication Data

US 2019/0169161 A1 Jun. 6, 2019

Related U.S. Application Data

(63) Continuation of application No. PCT/JP2017/029461, filed on Aug. 16, 2017.

(30) Foreign Application Priority Data

Sep. 15, 2016 (JP) ................. 2016-180462

(51) Int. Cl.
| | | |
|---|---|---|
| C07D 401/10 | (2006.01) | |
| C08F 34/00 | (2006.01) | |
| G02B 1/04 | (2006.01) | |
| C08F 2/50 | (2006.01) | |
| C08G 59/26 | (2006.01) | |

(52) U.S. Cl.
CPC .............. C07D 401/10 (2013.01); C08F 2/50 (2013.01); C08F 34/00 (2013.01); C08G 59/26 (2013.01); G02B 1/04 (2013.01); G02B 1/041 (2013.01)

(58) Field of Classification Search
None
See application file for complete search history.

(56) References Cited

U.S. PATENT DOCUMENTS

| 2008/0090026 A1 | 4/2008 | Bernatz et al. |
| 2015/0018445 A1 | 1/2015 | Iizuka et al. |

FOREIGN PATENT DOCUMENTS

| JP | 2006-188459 A | 7/2006 |
| JP | 2008-209533 A | 9/2008 |
| JP | 2009-126011 A | 6/2009 |
| JP | 2010-189534 A | 9/2010 |
| JP | 201 1-1 53248 A | 8/2011 |
| JP | 2011-157437 A | 8/2011 |
| JP | 4803331 B2 | 10/2011 |
| JP | 2013-028662 A | 2/2013 |
| JP | 2013-227390 A | 11/2013 |
| JP | 2013-227393 A | 11/2013 |
| JP | 5383994 B2 | 1/2014 |
| JP | 5898551 B2 | 4/2016 |
| WO | 2010/132029 A1 | 11/2010 |

OTHER PUBLICATIONS

R. E. Hughes et al., "Total Synthesis of d,l-Caryophyllene and d,l-Isocaryophyllene", Communications to the Editor, J. Am. Chem. Soc., vol. 85, pp. 362-363 (1963).
John E. Mc Murry et al., "Synthesis of Isocaryophyllene by Titanium-Induced Keto Ester Cyclization", Tetrahedron Letters, vol. 24, No. 18, pp. 1885-1888 (1983).
Chen et al., "Synthesis of a New Chiral Ligand, 6, 6'-Dihydroxy-5, 5'-Biquinoline (BIQOL) and Its Applications in the Asymmetric Addition of Diethylzinc to Aldehydes", Chirality, vol. 12, pp. 510-513 (2000).
Aoyama et al., "Kinetic Resolution of Axially Chiral 2,2'-Dihydroxy-1,1'-biaryls by Palladium-Catalyzed Alcoholysis", J. Am. Chem. Soc., vol. 127, pp. 10474-10475 (2005).
International Search Report dated Nov. 21, 2017 in International Application No. PCT/JP2017/029461.
Written Opinion dated Nov. 21, 2017 in International Application No. PCT/JP2017/029461.
English translation of International Preliminary Report on Patentability dated Jul. 17, 2018 in International Application No. PCT/JP2017/029461.

*Primary Examiner* — Zinna Northington Davis
(74) *Attorney, Agent, or Firm* — Sughrue Mion, PLLC

(57) ABSTRACT

A curable composition contains a compound represented by General Formula (1):

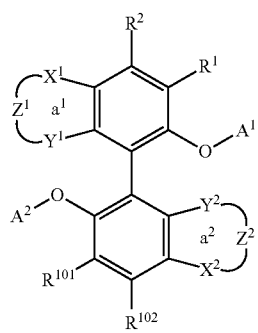

General Formula (1)

18 Claims, No Drawings

CURABLE COMPOSITION, CURED PRODUCT, OPTICAL MEMBER, LENS, AND COMPOUND

CROSS-REFERENCE TO RELATED APPLICATIONS

This application is a Continuation of PCT International Application No. PCT/JP2017/029461, filed on Aug. 16, 2017, which claims priority under 35 U.S.C. § 119(a) to Japanese Patent Application No. 2016-180462, filed on Sep. 15, 2016. Each of the above application(s) is hereby expressly incorporated by reference, in its entirety, into the present application.

BACKGROUND OF THE INVENTION

1. Field of the Invention

The present invention relates to a curable composition, a cured product, an optical member, a lens, and a compound.

2. Description of the Related Art

Conventionally, a glass material has been used for an optical member of an imaging module such as a camera, a video camera, a mobile phone with a camera, a video phone, or a door phone with a camera. The glass material has been preferably used since it has various optical properties and excellent environmental resistance. However, the glass material has a disadvantage in that weight reduction and miniaturization are not easy and workability or productivity is poor. In contrast, since a resin cured product can be produced in a massive amount and has excellent workability, the resin cured product has recently been used in various optical members.

In general, a resin cured product is molded by charging a curable composition into a mold for molding and curing the composition. Therefore, the curable composition used for the optical member is required to have good moldability in addition to exhibiting excellent optical properties after curing.

For example, JP4803331B discloses a compound having a (meth)acryloyloxy group at the terminal with an alkyleneoxy group as a linking group in a binaphthyl skeleton, and a curable resin composition containing such a compound. JP4803331B aims to obtain a low viscosity curable resin composition as a curable resin composition from which a cured product having a high refractive index can be molded.

Further, JP5383994B discloses a polymerizable compound having a biaryl structure and a liquid crystal display including such a polymerizable compound. The polymerizable compound having a biaryl structure may be, for example, a fused ring-containing compound in which a benzene ring, a cyclohexane ring, or a cyclohexene ring is fused to a biaryl skeleton is mentioned. In addition, JP5383994B does not disclose an exemplary compound in which a ring-constituting atom of the fused ring fused to the biaryl skeleton is a heteroatom.

SUMMARY OF THE INVENTION

However, as a result of investigation by the present inventors, it was found that, in a case where a cured product is formed using the polymerizable compound disclosed in JP4803331B and JP5383994B for a curable composition, the curable composition exhibited low viscosity and poor moldability. In addition, as a result of investigation by the present inventors, it was found that, in a case where the viscosity of the curable composition disclosed in JP4803331B and JP5383994B is increased to a level at which good moldability is exhibited, the refractive index of the obtained cured product is lowered.

Therefore, in order to solve such problems of the related arts, the present inventors have studied with an object to provide a curable composition which has excellent moldability and from which a cured product having a high refractive index can be molded, a cured product, an optical member, and a lens. In addition, the present inventors have studied with an object to provide a compound that is suitably used for a curable composition which has excellent moldability and is capable of forming a cured product having a high refractive index.

As a result of extensive studies to achieve the foregoing objects, the present inventors have found that use of a compound having a specific structure makes it possible to obtain a curable composition which has excellent moldability and from which a cured product having a high refractive index can be molded.

Specifically, the present invention has the following configuration.

[1] A curable composition comprising a compound represented by General Formula (1):

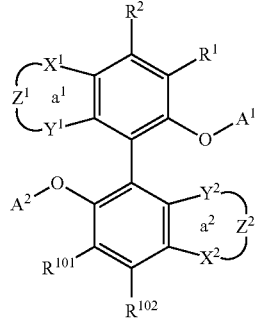

General Formula (1)

in General Formula (1), $X^1$, $X^2$, $Y^1$, and $Y^2$ each independently represent an oxygen atom, a sulfur atom, a nitrogen atom to which a hydrogen atom or a substituent may be bonded, or a carbon atom to which a hydrogen atom or a substituent may be bonded;

$Z^1$ is an atom or atomic group forming a 5- to 7-membered ring $a^1$ together with $X^1$—C=C—$Y^1$ and contains at least one selected from the group consisting of an oxygen atom, a sulfur atom, a nitrogen atom, and a carbon atom;

$Z^2$ is an atom or atomic group forming a 5- to 7-membered ring $a^2$ together with $X^2$—C=C—$Y^2$ and contains at least one selected from the group consisting of an oxygen atom, a sulfur atom, a nitrogen atom, and a carbon atom;

the ring $a^1$ has an oxygen atom, a sulfur atom, or a nitrogen atom as a ring skeleton atom and may further have a fused ring having two adjacent atoms among ring $a^1$ skeleton atoms of $X^1$, $Y^1$, and $Z^1$ as ring skeleton atoms;

the ring $a^2$ has an oxygen atom, a sulfur atom, or a nitrogen atom as a ring skeleton atom, and may further have a fused ring having two adjacent atoms among ring $a^2$ skeleton atoms of $X^2$, $Y^2$, and $Z^2$ as ring skeleton atoms;

$A^1$ and $A^2$ each independently represent a hydrogen atom or a substituent, and at least one of $A^1$ or $A^2$ represents a substituent containing at least one crosslinkable group selected from the group consisting of a vinyl group, an epoxy group, an oxetanyl group, and a (meth)acryloyl group; and $R^1$, $R^2$, $R^{101}$, and $R^{102}$ each independently represent a hydrogen atom, a halogen atom, a hydrocarbon group having 1 to 10 carbon atoms, or an alkoxy group having 1 to 10 carbon atoms.

The curable composition according to [1], in which $A^1$ and $A^2$ each independently represent a group represented by General Formula (2):

General Formula (2)

in General Formula (2), Alkylene represents an alkylene group having 2 to 6 carbon atoms, $L^1$ represents —O—, —S—, or —NH—, n1 represents an integer of 0 to 10, and P represents a hydrogen atom or a group represented by any one of General Formulae (P1) to (P4), and in a case where n1 is 2 or more, a plurality of Alkylene's and $L^1$'s each may be different from one another;

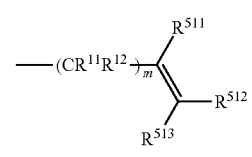

General Formula (P1)

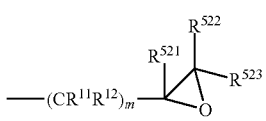

General Formula (P2)

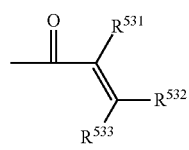

General Formula (P3)

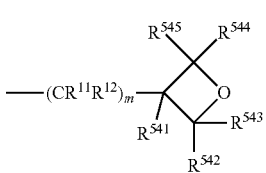

General Formula (P4)

in General Formulae (P1) to (P4), $R^{511}$, $R^{512}$, $R^{513}$, $R^{521}$, $R^{522}$, $R^{523}$, $R^{531}$, $R^{532}$, $R^{533}$, $R^{541}$, $R^{542}$, $R^{543}$, $R^{544}$, and $R^{545}$ each independently represent a hydrogen atom or an alkyl group, m represents an integer of 0 to 2, and $R^{11}$ and $R^{12}$ each independently represent a hydrogen atom or a substituent, and in a case where m is 2, a plurality of $R^{11}$'s and $R^{12}$'s each may be different from one another.

[3] The curable composition according to [1] or [2], in which the ring $a^1$ and the ring $a^2$ have a nitrogen atom as a ring skeleton atom.

[4] The curable composition according to [1], in which the compound represented by General Formula (1) is a compound represented by General Formula (3):

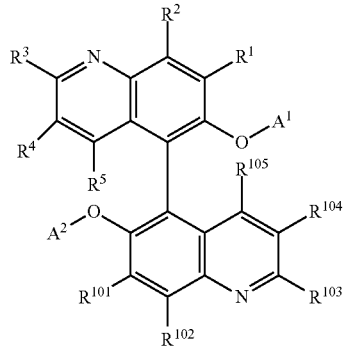

General Formula (3)

in General Formula (3), $A^1$ and $A^2$ each independently represent a hydrogen atom or a substituent, and at least one of $A^1$ or $A^2$ represents a substituent containing at least one crosslinkable group selected from the group consisting of a vinyl group, an epoxy group, an oxetanyl group, and a (meth)acryloyl group, and $R^1$ to $R^5$ and $R^{101}$ to $R^{105}$ each independently represent a hydrogen atom, a halogen atom, a hydrocarbon group having 1 to 10 carbon atoms, or an alkoxy group having 1 to 10 carbon atoms.

[5] The curable composition according to any one of [1] to [4], in which $A^1$ and $A^2$ are each independently a group represented by General Formula (4):

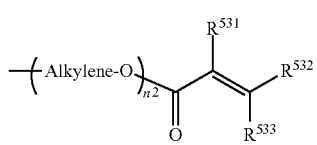

General Formula (4)

in General Formula (4), Alkylene represents an alkylene group having 2 to 6 carbon atoms, $R^{531}$, $R^{532}$, and $R^{533}$ each independently represent a hydrogen atom or an alkyl group, and n2 represents an integer of 0 to 10, and in a case where n2 is 2 or more, a plurality of Alkylene's may be different from one another.

[6] The curable composition according to any one of [1] to [5], further comprising at least one (meth)acrylate monomer different from the compound represented by General Formula (1) and at least one selected from the group consisting of a photoradical polymerization initiator and a thermal radical polymerization initiator.

[7] The curable composition according to any one of [1] to [6], in which the composition has a viscosity at 25° C. of 3000 mPa·s or more and less than 20000 mPa·s.

[8] A cured product of the curable composition according to any one of [1] to [7].

[9] An optical member comprising the cured product according to [8].

[10] A lens comprising the cured product according to [8].

[11] A compound represented by General Formula (1):

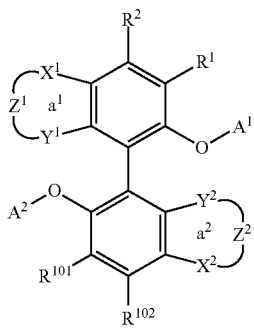

General Formula (1)

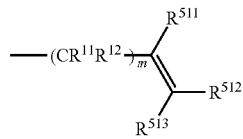

General Formula (P1)

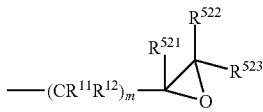

General Formula (P2)

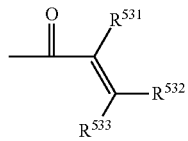

General Formula (P3)

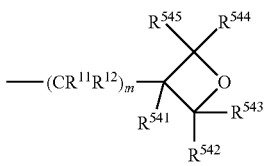

General Formula (P4)

in General Formula (1), $X^1$, $X^2$, $Y^1$, and $Y^2$ each independently represent an oxygen atom, a sulfur atom, a nitrogen atom to which a hydrogen atom or a substituent may be bonded, or a carbon atom to which a hydrogen atom or a substituent may be bonded;

$Z^1$ is an atom or atomic group forming a 5- to 7-membered ring $a^1$ together with $X^1$—C=C—$Y^1$ and contains at least one selected from the group consisting of an oxygen atom, a sulfur atom, a nitrogen atom, and a carbon atom;

$Z^2$ is an atom or atomic group forming a 5- to 7-membered ring $a^2$ together with $X^2$—C=C—$Y^2$ and contains at least one selected from the group consisting of an oxygen atom, a sulfur atom, a nitrogen atom, and a carbon atom;

the ring $a^1$ has an oxygen atom, a sulfur atom, or a nitrogen atom as a ring skeleton atom and may further have a fused ring having two adjacent atoms among ring $a^1$ skeleton atoms of $X^1$, $Y^1$, and $Z^1$ as ring skeleton atoms;

the ring $a^2$ has an oxygen atom, a sulfur atom, or a nitrogen atom as a ring skeleton atom, and may further have a fused ring having two adjacent atoms among ring $a^2$ skeleton atoms of $X^2$, $Y^2$, and $Z^2$ as ring skeleton atoms;

$A^1$ and $A^2$ each independently represent a hydrogen atom or a substituent, and at least one of $A^1$ or $A^2$ represents a substituent containing at least one crosslinkable group selected from the group consisting of a vinyl group, an epoxy group, an oxetanyl group, and a (meth)acryloyl group; and $R^1$, $R^2$, $R^{101}$, and $R^{102}$ each independently represent a hydrogen atom, a halogen atom, a hydrocarbon group having 1 to 10 carbon atoms, or an alkoxy group having 1 to 10 carbon atoms.

[12] The compound according to [11], in which $A^1$ and $A^2$ each independently represent a group represented by General Formula (2):

—(Alkylene-$L^1$)$_{n1}$—P

General Formula (2)

in General Formula (2), Alkylene represents an alkylene group having 2 to 6 carbon atoms, $L^1$ represents —O—, —S—, or —NH—, n1 represents an integer of 0 to 10, and P represents a hydrogen atom or a group represented by any one of General Formulae (P1) to (P4), and in a case where n1 is 2 or more, a plurality of Alkylene's and $L^1$'s each may be different from one another;

in General Formulae (P1) to (P4) $R^{511}$, $R^{512}$, $R^{513}$, $R^{521}$, $R^{522}$, $R^{523}$, $R^{531}$, $R^{532}$, $R^{533}$, $R^{541}$, $R^{542}$, $R^{543}$, $R^{544}$, and $R^{545}$ each independently represent a hydrogen atom or an alkyl group, m represents an integer of 0 to 2, and $R^{11}$ and $R^{12}$ each independently represent a hydrogen atom or a substituent, and in a case where m is 2, a plurality of $R^{11}$'s and $R^{12}$'s each may be different from one another.

[13] The compound according to [11] or [12], in which the ring $a^1$ and the ring $a^2$ have a nitrogen atom as a ring skeleton atom.

[14] The compound according to [11], in which the compound represented by General Formula (1) is a compound represented by General Formula (3):

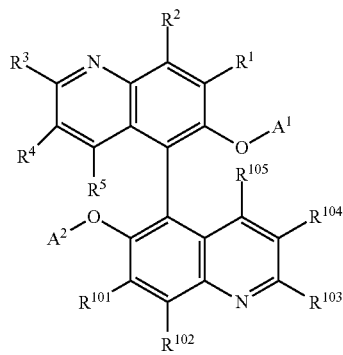

General Formula (3)

in General Formula (3), $A^1$ and $A^2$ each independently represent a hydrogen atom or a substituent, and at least one of $A^1$ or $A^2$ represents a substituent containing at least one crosslinkable group selected from the group consisting of a vinyl group, an epoxy group, an oxetanyl group, and a (meth)acryloyl group, and $R^1$ to $R^5$ and $R^{101}$ to $R^{105}$ each independently represent a hydrogen atom, a halogen atom, a hydrocarbon group having 1 to 10 carbon atoms, or an alkoxy group having 1 to 10 carbon atoms.

The compound according to any one of [11] to [14], in which $A^1$ and $A^2$ are each independently a group represented by General Formula (4):

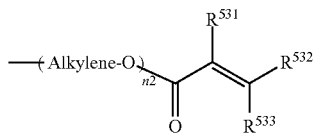

General Formula (4)

in General Formula (4), Alkylene represents an alkylene group having 2 to 6 carbon atoms, $R^{531}$, $R^{532}$, and $R^{533}$ each independently represent a hydrogen atom or an alkyl group, and n2 represents an integer of 0 to 10, and in a case where n2 is 2 or more, a plurality of Alkylene's may be different from one another.

According to the present invention, it is possible to obtain a curable composition which has excellent moldability and from which a cured product having a high refractive index can be molded. The cured product formed from the curable composition of the present invention is preferably used as an optical member and a lens. Further, according to the present invention, it is possible to obtain a compound that is suitably used for a curable composition which is a curable composition having excellent moldability and is capable of forming a cured product having a high refractive index.

DESCRIPTION OF THE PREFERRED EMBODIMENTS

Hereinafter, the present invention will be described in detail. The description of constituent elements described below can be made based on representative embodiments and specific examples, but the present invention is not limited to such embodiments. Numerical ranges expressed using "to" in the present specification mean a range including numerical values described before and after "to" as the lower limit and the upper limit.

In the present specification, "(meth)acrylate" refers to acrylate and methacrylate, and "(meth)acryloyl" refers to acryloyl and methacryloyl. The monomer in the present invention is a compound distinguished from oligomers and polymers and having a weight-average molecular weight of 1,000 or less.

In the indication of a group (atomic group) in the present specification, the indication not including substitution or unsubstitution includes those having a substituent and also those not having a substituent. For example, an "alkyl group" refers not only to an alkyl group not having a substituent (unsubstituted alkyl group) but also an alkyl group having a substituent (substituted alkyl group).

(Compound)

The present invention relates to a curable composition including a compound represented by General Formula (1). Further, the present invention relates to a compound represented by General Formula (1).

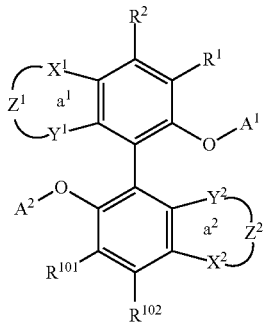

General Formula (1)

In General Formula (1), $X^1$, $X^2$, $Y^1$, and $Y^2$ each independently represent an oxygen atom, a sulfur atom, a nitrogen atom to which a hydrogen atom or a substituent may be bonded, or a carbon atom to which a hydrogen atom or a substituent may be bonded, and $Z^1$ is an atom or atomic group forming a 5- to 7-membered ring $a^1$ together with $X^1$—C=C—$Y^1$ and contains at least one selected from the group consisting of an oxygen atom, a sulfur atom, a nitrogen atom, and a carbon atom. $Z^2$ is an atom or atomic group forming a 5- to 7-membered ring $a^2$ together with $X^2$—C=C—$Y^2$ and contains at least one selected from the group consisting of an oxygen atom, a sulfur atom, a nitrogen atom, and a carbon atom. The ring $a^1$ has an oxygen atom, a sulfur atom, or a nitrogen atom as a ring skeleton atom and may further have a fused ring having two adjacent atoms among ring $a^1$ skeleton atoms of $X^1$, $Y^1$, and $Z^1$ as ring skeleton atom. The ring $a^2$ has an oxygen atom, a sulfur atom, or a nitrogen atom as a ring skeleton atom, and may further have a fused ring having two adjacent atoms among ring $a^2$ skeleton atoms of $X^2$, $Y^2$, and $Z^2$ as ring skeleton atoms.

$A^1$ and $A^2$ each independently represent a hydrogen atom or a substituent, and at least one of $A^1$ or $A^2$ represents a substituent containing at least one crosslinkable group selected from the group consisting of a vinyl group, an epoxy group, an oxetanyl group, and a (meth)acryloyl group.

$R^1$, $R^2$, $R^{101}$, and $R^{102}$ each independently represent a hydrogen atom, a halogen atom, a hydrocarbon group having 1 to 10 carbon atoms, or an alkoxy group having 1 to 10 carbon atoms.

In General Formula (1), $X^1$, $X^2$, $Y^1$, and $Y^2$ each independently represent an oxygen atom, a sulfur atom, a nitrogen atom to which a hydrogen atom or a substituent may be bonded, or a carbon atom to which a hydrogen atom or a substituent may be bonded. It is preferable that $X^1$, $X^2$, $Y^1$, and $Y^2$ are each independently a nitrogen atom or a carbon atom. In addition, it is particularly preferable that any one selected from $X^1$ or $Y^1$ is a nitrogen atom, and any one selected from $X^2$ or $Y^2$ is a nitrogen atom.

In the present specification, the substituent is not particularly limited, but examples thereof include substitutable substituents selected from a halogen atom, a halogenated alkyl group, an alkyl group, an alkenyl group, an acyl group, a hydroxy group, a hydroxyalkyl group, an alkoxy group, an aryl group, a heteroaryl group, an alicyclic group, a cyano group, an epoxy group, an oxetanyl group, a mercapto group, an amino group, and a (meth)acryloyl group. Such substituents may further have the above substituents.

$Z^1$ is an atom or atomic group forming a 5- to 7-membered ring $a^1$ together with $X^1$—C=C—$Y^1$ and contains at least one selected from an oxygen atom, a sulfur atom, a nitrogen atom, or a carbon atom. It is preferable that $Z^1$ is an atom or atomic group forming a 5- to 7-membered ring $a^1$ together with $X^1$—C=C—$Y^1$, and contains at least one selected from a nitrogen atom or a carbon atom. Similarly, $Z^2$ is an atom or atomic group forming a 5- to 7-membered ring $a^2$ together with $X^2$—C=C—$Y^2$ and contains at least one selected from an oxygen atom, a sulfur atom, a nitrogen atom, or a carbon atom. Like $Z^1$, it is preferable that $Z^2$ contains at least one selected from a nitrogen atom or a carbon atom.

The ring $a^1$ has an oxygen atom, a sulfur atom, or a nitrogen atom as a ring skeleton atom, and the ring $a^2$ has an oxygen atom, a sulfur atom, or a nitrogen atom as a ring skeleton atom. Above all, the ring $a^1$ preferably has a nitrogen atom as a ring skeleton atom, and the ring $a^2$ preferably has a nitrogen atom as a ring skeleton atom. The heteroatoms of the ring $a^1$ and the ring $a^2$ may be different from each other, but it is more preferable for both the ring $a^1$ and the ring $a^2$ to have a nitrogen atom as a ring skeleton atom.

The number of heteroatoms of each of the ring $a^1$ and the ring $a^2$ is preferably 2 or less and more preferably 1. By setting the number of heteroatoms of each of the ring $a^1$ and the ring $a^2$ to fall within the above range, it is possible to more effectively suppress coloration of a cured product in a case where the cured product is molded from the curable composition containing the compound represented by General Formula (1).

The ring $a^1$ may further have a fused ring having two adjacent atoms among the ring $a^1$ skeleton atoms of $X^1$, $Y^1$, and $Z^1$ as ring skeleton atoms, and the ring $a^2$ may further have a fused ring having two adjacent atoms among the ring $a^2$ skeleton atoms of $X^2$, $Y^2$, and $Z^2$ as ring skeleton atoms. In a case where the ring $a^1$ and the ring $a^2$ do not have a fused ring, the ring $a^1$ and the ring $a^2$ are each preferably a 5- or 6-membered ring and more preferably a 6-membered ring. In a case where the ring $a^1$ and the ring $a^2$ have a fused ring, the ring $a^1$ and the ring $a^2$ are each preferably a 5- or 6-membered ring and more preferably a 5-membered ring.

In addition, the ring $a^1$ may further have a fused ring having two adjacent atoms among the ring $a^1$ skeleton atoms of $X^1$, $Y^1$, and $Z^1$ as ring skeleton atoms, but it is preferable that the ring $a^1$ does not have such a fused ring. Similarly, the ring $a^2$ may further have a fused ring having two adjacent atoms among the ring $a^2$ skeleton atoms of $X^2$, $Y^2$, and $Z^2$ as ring skeleton atoms, but it is preferable that the ring $a^2$ does not have such a fused ring. By setting the ring $a^1$ and the ring $a^2$ to have no further fused rings, coloration of the cured product is easily suppressed. Further, the solubility of the compound represented by General Formula (1) and each component described later can be enhanced.

In General Formula (1), $R^1$, $R^2$, $R^{101}$, and $R^{102}$ each independently represent a hydrogen atom, a halogen atom, a hydrocarbon group having 1 to 10 carbon atoms, or an alkoxy group having 1 to 10 carbon atoms. Above all, $R^1$, $R^2$, $R^{101}$, and $R^{102}$ are each independently preferably a hydrogen atom or a hydrocarbon group having 1 to 10 carbon atoms, and more preferably a hydrogen atom.

In General Formula (1), $A^1$ and $A^2$ each independently represent a hydrogen atom or a substituent, and at least one of $A^1$ or $A^2$ represents a substituent containing at least one crosslinkable group selected from a vinyl group, an epoxy group, an oxetanyl group, or a (meth)acryloyl group. Among them, $A^1$ and $A^2$ are each independently preferably a substituent containing at least one crosslinkable group selected from a vinyl group, an epoxy group, an oxetanyl group, or a (meth)acryloyl group, and more preferably a group represented by General Formula (2).

General Formula (2)

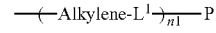

In General Formula (2), Alkylene represents an alkylene group having 2 to 6 carbon atoms, $L^1$ represents —O—, —S—, or —NH—, n1 represents an integer of 0 to 10, and P represents a hydrogen atom or a group represented by any one of General Formulae (P1) to (P4). In a case where n1 is 2 or more, a plurality of Alkylene's and $L^1$'s each may be different from one another.

General Formula (P1)

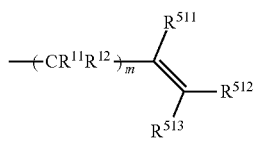

General Formula (P2)

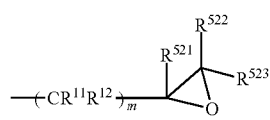

General Formula (P3)

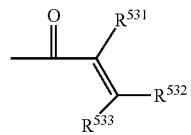

General Formula (P4)

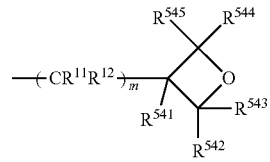

In General Formulae (P1) to (P4), $R^{511}$, $R^{512}$, $R^{513}$, $R^{521}$, $R^{522}$, $R^{523}$, $R^{531}$, $R^{532}$, $R^{533}$, $R^{541}$, $R^{542}$, $R^{543}$, $R^{544}$, and $R^{545}$ each independently represent a hydrogen atom or an alkyl group, m represents an integer of 0 to 2, and $R^{11}$ and $R^{12}$ each independently represent a hydrogen atom or a substituent. In a case where m is 2, a plurality of $R^{11}$'s and $R^{12}$'s each may be different from one another.

In General Formula (2), Alkylene represents an alkylene group having 2 to 6 carbon atoms, preferably an alkylene group having 2 to 4 carbon atoms, and more preferably an alkylene group having 2 carbon atoms. $L^1$ represents —O—, —S—, or —NH— and preferably —O—.

n1 represents an integer of 0 to 10, preferably represents an integer of 0 to 2, and more preferably 0 or 1.

In General Formulae (P1) to (P4), $R^{511}$, $R^{512}$, $R^{513}$, $R^{521}$, $R^{522}$, $R^{523}$, $R^{531}$, $R^{532}$, $R^{533}$, $R^{541}$, $R^{542}$, $R^{543}$, $R^{544}$, and $R^{545}$ each independently represent a hydrogen atom or an alkyl group, and in a case where $R^{511}$, $R^{512}$, $R^{513}$, $R^{521}$, $R^{522}$, $R^{523}$, $R^{531}$, $R^{532}$, $R^{533}$, $R^{541}$, $R^{542}$, $R^{543}$, $R^{544}$, and $R^{545}$ are alkyl groups, the alkyl group preferably has 1 to 6 carbon atoms, and more preferably 1 to 3. Above all, $R^{511}$, $R^{512}$, $R^{513}$, $R^{521}$, $R^{522}$, $R^{523}$, $R^{531}$, $R^{532}$, $R^{533}$, $R^{542}$, $R^{543}$, $R^{544}$, and $R^{545}$ are preferably hydrogen atoms, and $R^{541}$ is preferably an alkyl group having 1 to 3 carbon atoms.

In General Formulae (P1) to (P4), m represents an integer of 0 to 2 and preferably an integer of 0 or 1. $R^{11}$ and $R^{12}$ each independently represent a hydrogen atom or a substituent, preferably a hydrogen atom or an alkyl group, and more preferably a hydrogen atom. In a case where $R^{11}$ and $R^{12}$ are substituents, the same substituents as mentioned above can be mentioned as preferred substituents.

P is a hydrogen atom or a group represented by any one of General Formulae (P1) to (P4), more preferably a group represented by any one of General Formulae (P1) to (P4), and still more preferably a group represented by General Formula (P3). That is, $A^1$ and $A^2$ in General Formula (1) are each independently preferably a substituent containing a (meth)acryloyl group, and $A^1$ and $A^2$ are each independently more preferably a group represented by General Formula (4). By setting $A^1$ and $A^2$ to be a group represented by General Formula (4), the viscosity of the curable composition can be increased more efficiently. Further, by setting $A^1$ and $A^2$ to be a group represented by General Formula (4), it is possible to improve the surface transferability upon molding a cured product from the curable composition and therefore it is easy to mold a cured product in which occurrence of fine irregularities (wrinkles) and cracks is suppressed.

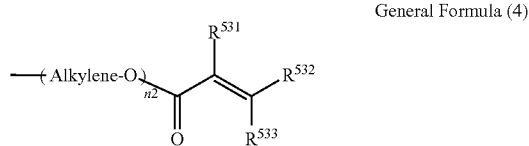

General Formula (4)

In General Formula (4), Alkylene represents an alkylene group having 2 to 6 carbon atoms, $R^{531}$, $R^{532}$, and $R^{533}$ each independently represent a hydrogen atom or an alkyl group, and n2 represents an integer of 0 to 10. In a case where n2 is 2 or more, a plurality of Alkylene's may be different from one another.

Alkylene represents an alkylene group having 2 to 6 carbon atoms, preferably an alkylene group having 2 to 4 carbon atoms, and more preferably an alkylene group having 2 carbon atoms. n2 represents an integer of 0 to 10, preferably an integer of 0 to 2, and more preferably 0 or 1.

In General Formula (1), $A^1$ and $A^2$ may be different groups, but $A^1$ and $A^2$ are preferably the same groups.

The compound represented by General Formula (1) is preferably a compound represented by General Formula (3).

General Formula (3)

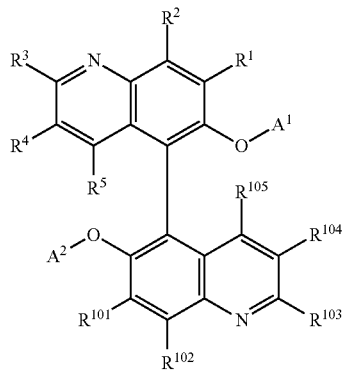

In General Formula (3), $A^1$ and $A^2$ each independently represent a hydrogen atom or a substituent, and at least one of $A^1$ or $A^2$ represents a substituent containing at least one crosslinkable group selected from the group consisting of a vinyl group, an epoxy group, an oxetanyl group, and a (meth)acryloyl group. $R^1$ to $R^5$ and $R^{101}$ to $R^{105}$ each independently represent a hydrogen atom, a halogen atom, a hydrocarbon group having 1 to 10 carbon atoms, or an alkoxy group having 1 to 10 carbon atoms.

The preferred ranges of $A^1$ and $A^2$ in General Formula (3) are the same as the preferred ranges of $A^1$ and $A^2$ in General Formula (1).

The preferred ranges of $R^1$, $R^2$, $R^{101}$, and $R^{102}$ in General Formula (3) are the same as the preferable ranges of $R^1$, $R^2$, $R^{101}$, and $R^{102}$ in General Formula (1).

In General Formula (3), $R^3$ to $R^5$ and $R^{103}$ to $R^{105}$ each independently represent a hydrogen atom, a halogen atom, a hydrocarbon group having 1 to 10 carbon atoms, or an alkoxy group having 1 to 10 carbon atoms. Above all, $R^3$ to $R^5$ and $R^{103}$ to $R^{105}$ are each independently preferably a hydrogen atom or a hydrocarbon group having 1 to 10 carbon atoms, and more preferably a hydrogen atom.

Specific examples of the compound represented by General Formula (1) preferably used in the present invention are listed below, but the compounds are not limited to the following compounds. In the following specific examples, as shown in the following structural formula, the constitution of the compound represented by General Formula (1) is divided into the partial structures of A and B, and the respective partial structures are listed. That is, specific examples of the compound represented by General Formula (1) include structures in which the structures listed as the partial structure A and the partial structure B are combined.

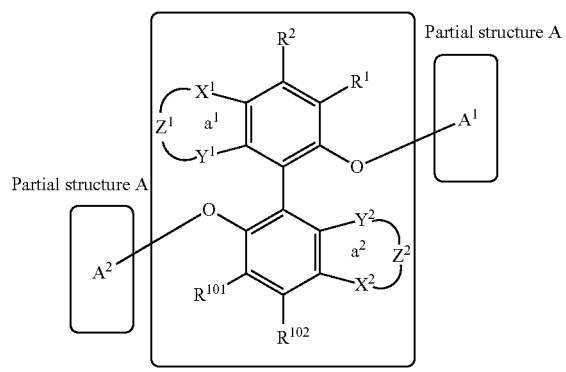

Specific Examples of Partial Structure A

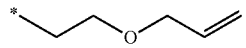

(A-1)

(A-2)

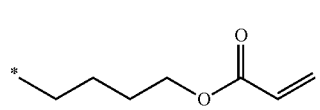

(A-3)

13
-continued
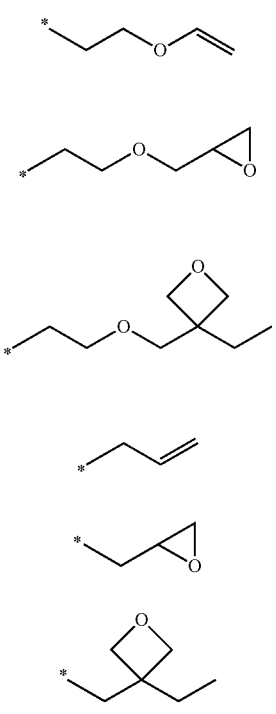
(A-4)
(A-5)
(A-6)
(A-7)
(A-8)
(A-9)
In the structural formulae of the specific examples of the partial structure A, # represents a connecting portion with the partial structure B. Note that each of the two partial structures A may have a different structure.
Specific Examples Structures B
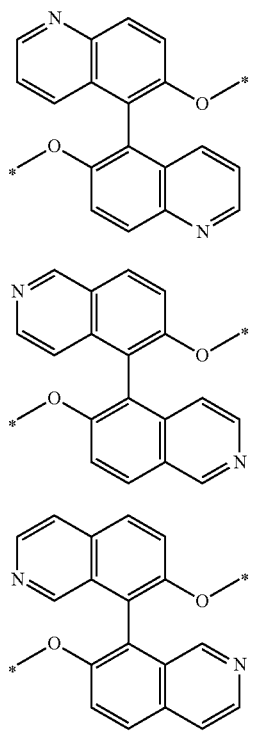
(B-1)
(B-2)
(B-3)
14
-continued
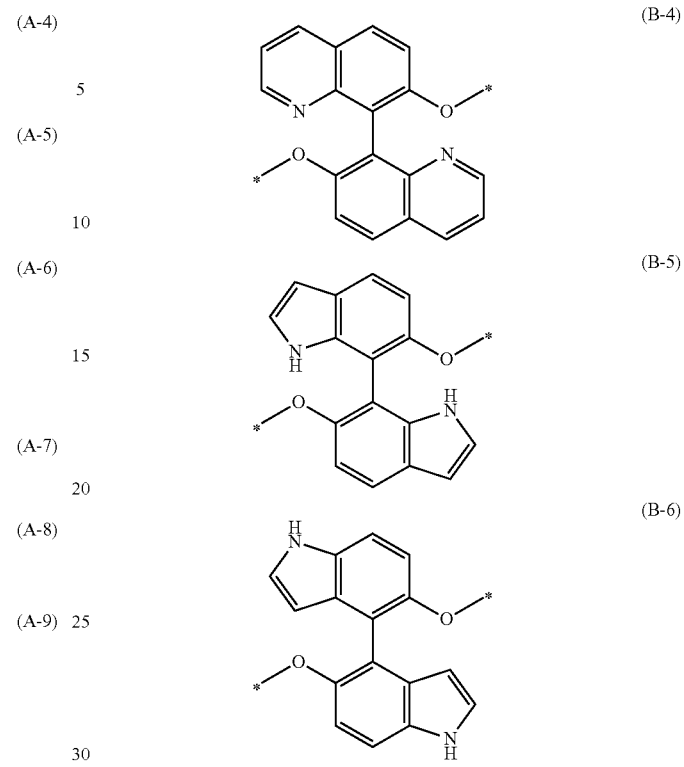
(B-4)
(B-5)
(B-6)
(B-7)
(B-8)
(B-9)

-continued

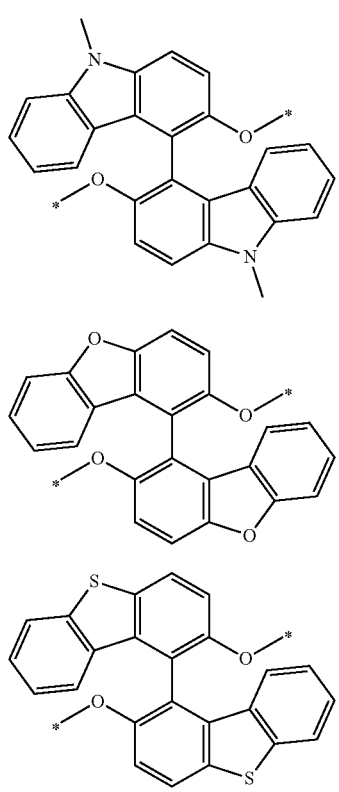

(B-10)

(B-11)

(B-12)

In the structural formulae of the specific examples of the partial structure B, * represents a connecting portion with the partial structure A.

Among them, the compound represented by General Formula (1) is preferably any one of Compounds (1) to (20) shown below.

TABLE 1

|  | Partial structure A | Partial structure B |
| --- | --- | --- |
| Compound (1) | A-1 | B-1 |
| Compound (2) | A-2 | B-1 |
| Compound (3) | A-3 | B-1 |
| Compound (4) | A-4 | B-1 |
| Compound (5) | A-5 | B-1 |
| Compound (6) | A-6 | B-1 |
| Compound (7) | A-7 | B-1 |
| Compound (8) | A-8 | B-1 |
| Compound (9) | A-9 | B-1 |
| Compound (10) | A-2 | B-2 |
| Compound (11) | A-2 | B-3 |
| Compound (12) | A-2 | B-4 |
| Compound (13) | A-2 | B-5 |
| Compound (14) | A-2 | B-6 |
| Compound (15) | A-2 | B-7 |
| Compound (16) | A-2 | B-8 |
| Compound (17) | A-2 | B-9 |
| Compound (18) | A-2 | B-10 |
| Compound (19) | A-2 | B-11 |
| Compound (20) | A-2 | B-12 |

Among the above structures, the partial structure A is preferably any one of (A-1) to (A-4), more preferably (A-1), (A-2), or (A-3), and particularly preferably (A-2). The partial structure B is preferably any one of (B-1) to (B-4), more preferably (B-1) or (B-4), and particularly preferably (B-1).

The molecular weight of the compound represented by General Formula (1) is preferably 350 to 1,000, more preferably 400 to 900, and particularly preferably 450 to 800.

The method for obtaining the compound represented by General Formula (1) is not particularly limited, and the compound may be commercially available or may be produced by synthesis. In a case of production by synthesis, the method for producing the compound represented by General Formula (1) is not particularly limited and the compound can be synthesized by known methods and methods described in the Examples.

(Curable composition)

The present invention relates to a curable composition containing the compound represented by General Formula (1). Since the curable composition according to the embodiment of the present invention contains a compound having a specific structure, the curable composition exhibits excellent moldability and has high production efficiency in a case of molding a cured product from the curable composition. This is believed to be due to the fact that the curable composition according to the embodiment of the present invention has a viscosity of a certain level or more suitable for molding. Since the curable composition according to the embodiment of the present invention contains the compound represented by General Formula (1), the viscosity of the curable composition can be increased and therefore the viscosity suitable for molding can be obtained. Thereby, leakage of the curable composition from the molding mold during molding (resin leakage) can be suppressed, and therefore the production efficiency of the cured product can be enhanced. In addition, by controlling the viscosity of the curable composition within a suitable range, the transferability and mold followability of the cured product can be enhanced and therefore the cured product in which occurrence of fine irregularities (wrinkles) and cracks is suppressed can be obtained. Further, contamination of process equipment caused by leakage of the curable composition out of the mold can be suppressed.

Since the curable composition according to the embodiment of the present invention contains the compound represented by General Formula (1), a cured product having a high refractive index can be molded. Further, in the present invention, since the curable composition has a viscosity of a certain level or more suitable for molding, the addition amount of other components (for example, a thickener to be described later) exhibiting a thickening effect can be reduced. Conventionally, in order to make the viscosity of the curable composition suitable for molding, a thickener was sometimes added to the curable composition. In a case where the amount of the thickener added is large, the content of the compound capable of exhibiting a high refractive index decreases and therefore there remains a problem that a sufficiently high refractive index cannot be achieved. However, in the present invention, the viscosity of the curable composition can be increased since the composition contains the compound represented by General Formula (1). This makes it possible to mold a cured product from the curable composition without decreasing the amount of the thickener to be added or without adding the thickener at all. That is, in the present invention, in addition to containing the compound represented by General Formula (1) capable of exhibiting a high refractive index, the content of the compound represented by General Formula (1) can be increased, so that the refractive index of the cured product can be more effectively increased.

The viscosity of the curable composition according to the embodiment of the present invention at 25° C. is preferably 1,000 mPa·s or more, more preferably 2,000 mPa·s or more, still more preferably 3,000 mPa·s or more, even more preferably 4,000 mPa·s or more, particularly preferably 4,500 mPa·s or more, and most preferably 5,000 mPa·s or more. Further, the viscosity of the curable composition at 25° C. is preferably 20,000 mPa·s or less, more preferably 15,000 mPa·s or less, still more preferably 13,000 mPa·s or less, and particularly preferably 10,000 mPa·s or less. The above viscosity is a viscosity in a state in which a thickener (such as a polymer exhibiting a thickening action) is not added to the curable composition. By setting the viscosity of the curable composition at 25° C. within the above range, it is possible to improve the moldability at the time of molding the cured product from the curable composition. Further, by setting the viscosity of the curable composition at 25° C. within the above range, the content of the compound represented by General Formula (1) can be increased, so that the refractive index of the cured product can be more effectively increased.

The content of the compound represented by General Formula (1) in the curable composition is preferably 20% by mass or more, more preferably 40% by mass or more, still more preferably 50% by mass or more, even more preferably 60% by mass or more, and particularly preferably 61% by mass or more, with respect to the total mass of the curable composition. Further, the content of the compound represented by General Formula (1) is preferably 94% by mass or less and more preferably 85% by mass or less, with respect to the total mass of the curable composition. By setting the content of the compound within the above range, the viscosity of the curable composition can be adjusted to a suitable range and therefore the viscosity of the curable composition can be easily adjusted to a desired range, so that it is possible to enhance the moldability at the time of molding the cured product. Further, by setting the content of the compound within the above range, the refractive index of the cured product can be more effectively enhanced. Further, it is possible to improve the surface transferability, and it is possible to suppress occurrence of fine irregularities (wrinkles) and cracks on the surface of the cured product.

Two or more compounds represented by General Formula (1) may be contained in the curable composition. In a case where two or more compounds represented by General Formula (1) are contained, the total content thereof is preferably within the above range.

The curable composition according to the embodiment of the present invention preferably contains the following components in addition to the above-mentioned compounds. For example, the curable composition preferably further contains at least one (meth)acrylate monomer different from the compound represented by General Formula (1), and at least one selected from a photoradical polymerization initiator or a thermal radical polymerization initiator. In addition, the curable composition according to the embodiment of the present invention may further contain a non-conjugated vinylidene group-containing compound.

((Meth)Acrylate Monomer)

The curable composition according to the embodiment of the present invention preferably contains at least one (meth)acrylate monomer different from the compound represented by General Formula (1). The (meth)acrylate monomer may be a polyfunctional (meth)acrylate monomer having two or more (meth)acryloyl groups in the molecule, but it is preferably a monofunctional (meth)acrylate monomer having one (meth)acryloyl group in the molecule.

The viscosity of the (meth)acrylate monomer at 25° C. is preferably less than 2,000 mPa·s. The viscosity at 25° C. of the (meth)acrylate monomer is preferably less than 1,500 mPa·s, more preferably less than 1,000 mPa·s, still more preferably less than 500 mPa·s, and particularly preferably less than 200 mPa·s. The viscosity at 25° C. of the (meth) acrylate monomer is a value measured using a rheometer (RS600, manufactured by HAAKE GmbH) under conditions of 25° C. and a shear rate of 10 s$^{-1}$.

Examples of the monofunctional (meth)acrylate monomer used in the present invention include adamantyl (meth) acrylates such as 1-adamantyl (meth)acrylate, norbornyl (meth)acrylates such as isobornyl (meth)acrylate, tricyclodecane (meth)acrylates such as tricyclo [5,2,1,0$^{2,6}$]decan-8-yl acrylate, 2-ethyl-2-butylpropanediol (meth)acrylate, 2-ethylhexyl (meth)acrylate, 2-ethylhexylcarbitol (meth) acrylate, 2-hydroxybutyl (meth)acrylate, 2-hydroxyethyl (meth)acrylate, 2-hydroxypropyl (meth)acrylate, 2-methoxyethyl (meth)acrylate, 3-methoxybutyl (meth) acrylate, 4-hydroxybutyl (meth)acrylate, benzyl (meth)acrylate, butanediol mono(meth)acrylate, butoxyethyl (meth) acrylate, butyl (meth)acrylate, cetyl (meth)acrylate, ethylene oxide (EO)-modified cresol (meth)acrylate, dipropylene glycol (meth)acrylate, ethoxylated phenyl (meth)acrylate, ethyl (meth)acrylate, isoamyl (meth)acrylate, isobutyl (meth) acrylate, isooctyl (meth)acrylate, cyclohexyl (meth)acrylate, dicyclopentanyl (meth)acrylate, dicyclopentanyloxy ethyl (meth)acrylate, isomyristyl (meth)acrylate, lauryl (meth) acrylate, methoxydipropylene glycol (meth)acrylate, methoxytripropylene glycol (meth)acrylate, methoxypolyethylene glycol (meth)acrylate, methoxytriethylene glycol (meth)acrylate, methyl (meth)acrylate, neopentyl glycol benzoate (meth)acrylate, nonylphenoxypolyethylene glycol (meth)acrylate, nonylphenoxypolypropylene glycol (meth) acrylate, octyl (meth)acrylate, paracumylphenoxyethylene glycol (meth)acrylate, epichlorohydrin (ECH)-modified phenoxy(meth)acrylate, phenoxyethyl (meth)acrylate, phenoxydiethylene glycol (meth)acrylate, phenoxyhexaethylene glycol (meth)acrylate, phenoxytetraethylene glycol (meth)acrylate, stearyl (meth)acrylate, EO-modified succinic acid (meth)acrylate, tert-butyl (meth)acrylate, tribromophenyl (meth)acrylate, EO-modified tribromophenyl (meth)acrylate, and tridodecyl (meth)acrylate.

The (meth)acrylate monomer is preferably a (meth)acrylate monomer containing an aryl group or a heteroaryl group. Among them, the (meth)acrylate monomer is more preferably a monofunctional (meth)acrylate monomer containing an aryl group or a heteroaryl group and still more preferably a monofunctional (meth)acrylate monomer containing an aryl group. Use of a (meth)acrylate monomer containing an aryl group or a heteroaryl group can lead to a reduction of an Abbe's number of a cured product. Further, use of a (meth)acrylate monomer containing an aryl group or a heteroaryl group readily brings about uniform mixing of the (meth)acrylate monomer in the curable composition, so the transparency and durability of the cured product can be more effectively enhanced.

Examples of the (meth)acrylate monomer containing an aryl group or a heteroaryl group include benzyl (meth) acrylate, EO-modified cresol (meth)acrylate, ethoxylated phenyl (meth)acrylate, nonylphenoxypolyethylene glycol (meth)acrylate, nonylphenoxypolypropylene glycol (meth) acrylate, paracumylphenoxyethylene glycol (meth)acrylate, ECH-modified phenoxy(meth)acrylate, phenoxyethyl (meth)acrylate, phenoxydiethylene glycol (meth)acrylate, phenoxyhexaethylene glycol (meth)acrylate, phenoxytetraethylene glycol (meth)acrylate, tribromophenyl (meth)acrylate, EO-modified tribromophenyl (meth)acrylate, O-phenylphenol (meth)acrylate, and O-phenylphenol EO-modified (meth)acrylate. Among them, benzyl (meth)acrylate, phenoxyethyl (meth)acrylate, O-phenylphenol (meth)acrylate, and O-phenylphenol EO-modified (meth)acrylate are more preferable, benzyl (meth)acrylate and phenoxyethyl (meth)acrylate are particularly preferable, and benzyl acrylate and phenoxyethyl acrylate are particularly more preferable.

The (meth)acrylate monomer may be an alicyclic (meth)acrylate monomer. The alicyclic (meth)acrylate monomer may be one in which one (meth)acryloyl group is bonded to an aliphatic ring directly or through a divalent linking group, or one in which two or more (meth)acryloyl groups are bonded to an aliphatic ring directly or through a divalent linking group. Among them, a monofunctional (meth)acrylate monomer in which one (meth)acryloyl group is directly bonded to an aliphatic ring is preferably used.

The aliphatic ring may have a monocyclic structure or a polycyclic structure in which two or more aliphatic rings are linked or fused, and may contain a bridged ring hydrocarbon. In addition, the aliphatic ring may consist of only a carbon atom and a hydrogen atom, or may contain a heteroatom in addition to a carbon atom and a hydrogen atom. The number of carbon atoms in the aliphatic ring is not particularly limited, but it is preferably 6 to 20, more preferably 7 to 15, and still more preferably 7 to 10. Specifically, the aliphatic ring is preferably tricyclodecane, adamantane, norbornane, cyclohexane, or norbornene, more preferably tricyclodecane, adamantane, or norbornane, and still more preferably tricyclodecane.

As the (meth)acrylate monomer which can be preferably used in the present invention, for example, the following compounds can be listed.

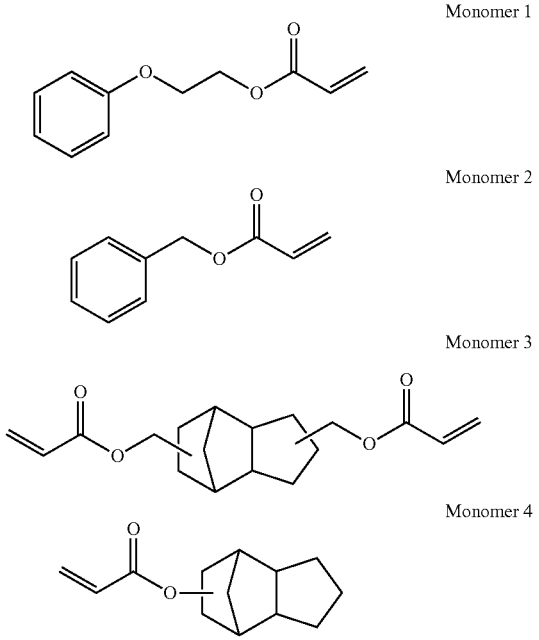

Monomer 1

Monomer 2

Monomer 3

Monomer 4

The method of obtaining the (meth)acrylate monomer is not particularly limited, and the compound may be commercially available or may be produced by synthesis. In a case of commercially obtaining the compound, for example, VISCOAT #192 PEA (Monomer 1) (manufactured by Osaka Organic Chemical Industry Ltd.), VISCOAT #160 BZA (Monomer 2) (manufactured by Osaka Organic Chemical Industry Ltd.), A-DCP (Monomer 3) (manufactured by Shin-Nakamura Chemical Co., Ltd.), or FA-513AS (Monomer 4) (manufactured by Hitachi Chemical Co., Ltd.) may be preferably used. The viscosity of Monomer 1 at 25° C. and a shear rate of 10 s$^{-1}$ is 9 mPa·s, the viscosity of Monomer 2 at 25° C. and a shear rate of 10 s$^{-1}$ is 8 mPa·s, the viscosity of Monomer 3 at 25° C. and a shear rate of 10 s$^{-1}$ is 120 mPa·s, and the viscosity of Monomer 4 at 25° C. and a shear rate of 10 s$^{-1}$ is 12 mPa·s.

The content of the (meth)acrylate monomer is preferably 5% to 80% by mass, more preferably 5% to 50% by mass, and still more preferably 5% to 40% by mass, with respect to the total mass of the curable composition.

(Non-Conjugated Vinylidene Group-Containing Compound)

The curable composition according to the embodiment of the present invention may further contain a non-conjugated vinylidene group-containing compound represented by General Formula (13) or General Formula (14).

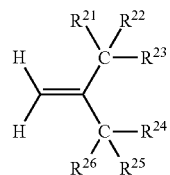

General Formula (13)

In General Formula (13), $R^{21}$ to $R^{26}$ each independently represent a substituent, at least one of $R^{21}, \ldots,$ or $R^{26}$ forms a ring, or at least two of $R^{21}$ to $R^{26}$ are bonded to each other to form a ring. However, the non-conjugated vinylidene group-containing compound represented by General Formula (13) does not contain a (meth)acryloyl group.

The substituent represented by $R^{21}$ to $R^{26}$ in General Formula (13) is not particularly limited and examples thereof include a hydrogen atom, a halogen atom, a halogenated alkyl group, an alkyl group, an alkenyl group, an acyl group, a hydroxy group, a hydroxyalkyl group, an aromatic ring group, a heteroaromatic ring group, and an alicyclic group. Among them, $R^{21}$ to $R^{26}$ are preferably a hydrogen atom, an alkyl group, or an alkenyl group, and more preferably a hydrogen atom, an alkyl group having 1 to 5 carbon atoms, or an alkenyl group having 2 to 5 carbon atoms.

The ring formed by $R^{21}$ to $R^{26}$ may be an aromatic ring or a heteroaromatic ring, and may also be a non-aromatic ring. Above all, the ring to be formed by $R^{21}$ to $R^{26}$ is preferably a non-aromatic ring and more preferably a non-aromatic hydrocarbon ring. The ring to be formed by $R^{21}$ to $R^{26}$ may further have a substituent, and for example, the substituent is preferably an alkyl group having 1 to 5 carbon atoms and more preferably a methyl group, an ethyl group, an n-propyl group, or an isopropyl group. In a case where the ring to be formed by $R^{21}$ to $R^{26}$ has additional substituents, the substituents may be bonded to each other to form a fused ring.

The non-conjugated vinylidene group-containing compound represented by General Formula (13) may have one ring or multiple rings formed by $R^{21}$ to $R^{26}$ therein. In a case where the compound has multiple rings formed by $R^{21}$ to $R^{26}$, the rings may be multiple rings independent of each other, or those independent multiple rings may be fused to form a fused ring, or in a case where one ring has additional substituents, the substituents may be bonded to each other to form a fused ring. Above all, the ring to be formed by $R^{21}$ to $R^{26}$ is more preferably a fused ring formed through fusion of multiple rings; and in a case where one ring has additional substituents, particularly preferably, the substituents are bonded to each other to form a fused ring. In this description, an aspect where two rings form a spiro-fusion is also within the scope of the concept of the fused ring here. Of the carbon atom to which $R^{21}$ and $R^{22}$ are bonded and the carbon atom to which $R^{25}$ and $R^{26}$ are bonded, one carbon atom is preferably an asymmetric carbon atom.

The non-conjugated vinylidene group-containing compound represented by General Formula (13) preferably contains a fused ring formed through fusion of 2 to 5 rings and more preferably a fused ring formed through fusion of 2 or 3 rings. In addition, the number of the ring-constituting atoms of each ring constituting the fused ring is preferably 3 to 10, more preferably 3 to 9, and particularly preferably 4 to 9.

Of $R^{21}$ to $R^{26}$, (A) at least one forms a ring, or (B) at least two are bonded to each other to form a ring. Of $R^{21}$ to $R^{26}$ in the non-conjugated vinylidene group-containing compound, case (B) is preferred where at least two are bonded to each other to form a ring. In this case, it is preferred that the non-conjugated vinylidene group-containing compound is represented by General Formula (14).

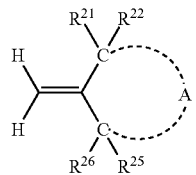

General Formula (14)

In General Formula (14), $R^{21}$, $R^{22}$, $R^{25}$, and $R^{26}$ each independently represent a substituent, and A represents an atomic group necessary for forming a cyclic structure.

In General Formula (14), the preferred ranges of substituents represented by $R^{21}$, $R^{22}$, $R^{25}$, and $R^{26}$ are the same as the preferred ranges of $R^{21}$ to $R^{26}$ in General Formula (13). In addition, $R^{21}$, $R^{22}$, $R^{25}$, and $R^{26}$ may further be bonded to one another to form a ring, and the ring may further have a substituent.

Preferably, of the pair of $R^{21}$ and $R^{22}$ or the pair of $R^{25}$ and $R^{26}$, at least one of the two substituents in any one pair alone is a hydrogen atom, and more preferably, both the two substituents in any one pair alone are hydrogen atoms.

Also preferably, $R^{21}$ and $R^{22}$ are each independently a hydrogen atom or a hydrocarbon group having 1 to 5 carbon atoms, and the hydrocarbon group having 1 to 5 carbon atoms does not form a ring. Of $R^{21}$ and $R^{22}$, preferably, one alone is a hydrogen atom or a hydrocarbon group having 1 to 5 carbon atoms, and the hydrocarbon group having 1 to 5 carbon atoms does not form a ring.

In General Formula (14), A represents an atomic group necessary for forming a cyclic structure, and the cyclic structure is not particularly limited and may be any known cyclic structure. Examples of the cyclic structure include an alicyclic ring (non-aromatic hydrocarbon ring), an aromatic ring, a heterocyclic ring, and a lactone ring containing —CO—. Of those, A is preferably an atomic group necessary for forming a alicyclic ring having 4 to 10 carbon atoms including the carbon atoms bonded to A in General Formula (14) and the carbon atom constituting the non-conjugated vinylidene group, and particularly preferably an atomic group necessary for forming an alicyclic ring having 5 to 9 carbon atoms including the carbon atoms bonding to A in General Formula (14) and the carbon atom constituting the non-conjugated vinylidene group. The alicyclic ring may have an additional substituent, and the preferred range of the substituent is the same as that of the additional substituent that the ring to be formed by $R^{21}$, $R^{22}$, $R^{25}$, and $R^{26}$ may have. A may be an unsaturated alicyclic ring or a saturated alicyclic ring, but it is preferred that at least one unsaturated bond is contained in the entire non-conjugated vinylidene group-containing compound represented by General Formula (14). A may further form a fused ring along with the substituent represented by $R^{21}$, $R^{22}$, $R^{25}$, and $R^{26}$.

According to the present invention, in General Formula (14), it is particularly preferred that $R^{21}$, $R^{22}$, $R^{25}$, and $R^{26}$ each independently represent a substituent consisting of only hydrogen atoms and carbon atoms, and A represents an alicyclic (non-aromatic hydrocarbon) structure.

In the present invention, the non-conjugated vinylidene group-containing compound represented by General Formula (13) or (14) preferably has an additional alkenyl group in addition to the vinylidene group (non-conjugated vinylidene group). The position of the vinylidene group other than the non-conjugated vinylidene group contained in the non-conjugated vinylidene group-containing compound represented by General Formula (13) or (14) is not particularly limited. Among them, the non-conjugated vinylidene group-containing compound represented by General Formula (13) or (14) preferably has a vinylidene group other than the non-conjugated vinylidene group on the ring formed by $R^{21}$, $R^{22}$, $R^{25}$, and $R^{26}$. That is, the ring formed by $R^{21}$, $R^{22}$, $R^{25}$, and $R^{26}$ particularly preferably contains at least one unsaturated hydrocarbon ring, and more particularly preferably an unsaturated hydrocarbon ring that has only one double bond.

The molecular weight of the non-conjugated vinylidene group-containing compound is preferably 100 to 400, more preferably 120 to 350, and particularly preferably 130 to 300.

The method of obtaining the non-conjugated vinylidene group-containing compound is not particularly limited, and the compound may be commercially available or may be produced by synthesis. In a case of commercially obtaining the compound, for example, β-caryophyllene (manufactured by Inoue Perfumery Co., Ltd.) may be preferably used.

In a case of producing the compound by synthesis, the method for producing the non-conjugated vinylidene group-containing compound represented by General Formula (13) or (14) is not particularly limited and the compound may be synthesized by any known method. For example, in a case of synthesizing β-caryophyllene which can be preferably used in the present invention, the compound may be synthesized according to the method described in J. Am. Chem. Soc. 85, 362 (1964), Tetrahedron Lette., 24, 1885 (1983), or the like.

The content of the non-conjugated vinylidene group-containing compound is preferably 0.5% to 30% by mass, more preferably 1% to 25% by mass, and still more preferably 2% to 20% by mass, with respect to the total mass of the curable composition.

<Photoradical Polymerization Initiator>

The curable composition according to the embodiment of the present invention preferably contains at least one selected from the group consisting of a photoradical polymerization initiator and a thermal radical polymerization initiator. The photoradical polymerization initiator is not particularly limited and may be any known photoradical polymerization initiator.

Specifically, the following compounds can be used as the photoradical polymerization initiator. Examples of the photoradical polymerization initiator include bis(2,6-dimethoxybenzoyl)-2,4,4-trimethylpentylphosphine oxide, bis(2,6-dimethylbenzoyl)-2,4,4-trimethylpentylphosphine oxide, bis(2,4,6-trimethylbenzoyl)-2,4,4-trimethylpentylphosphine oxide, bis(2,6-dichlorobenzoyl)-2,4,4-trimethylpentylphosphine oxide, 1-phenyl-2-hydroxy-2-methylpropan-1-one, 1-hydroxycyclohexyl phenyl ketone, 1-(4-isopropylphenyl)-2-hydroxy-2-methylpropan-1-one, 1,2-diphenylethanedione, methylphenyl glyoxylate, 1-[4-(2-hydroxyethoxy)-phenyl]-2-hydroxy-2-methyl-1-propan-1-one, 2-hydroxy-1-{4-[4-(2-hydroxy-2-methyl-propionyl)-benzyl]phenyl}-2-methyl-propan-1-one, 2,2-dimethoxy-1,2-diphenylethan-1-one, 2-methyl-1-(4-methylthiophenyl)-2-morpholinopropan-1-one, 2-benzyl-2-dimethylamino-1-(4-morpholinophenyl)butanone-1,2,4,6-trimethylbenzoyl-diphenyl-phosphine oxide, and bis(2,4,6-trimethylbenzoyl)-phenylphosphine oxide.

Of the above, in the present invention, BASF's IRGACURE 184 (1-hydroxycyclohexyl phenyl ketone), IRGACURE 819 (bis(2,4,6-trimethylbenzoyl)-phenylphosphine oxide), 1-[4-(2-hydroxyethoxy)-phenyl]-2-hydroxy-2-methyl-1-propan-1-one, 2-methyl-1-(4-methylthiophenyl)-2-morpholinopropan-1-one, or 2,2-dimethoxy-1,2-diphenylethan-1-one may be preferably used as the photoradical polymerization initiator.

The content of the photoradical polymerization initiator is preferably 0.01% to 5.0% by mass, more preferably 0.05% to 1.0% by mass, and still more preferably 0.05% to 0.5% by mass, with respect to the total mass of the curable composition.

(Thermal Radical Polymerization Initiator)

The curable composition according to the embodiment of the present invention preferably contains a thermal radical polymerization initiator. By adding a thermal radical polymerization initiator to the curable composition in advance, it is possible to mold a cured product having high heat resistance by thermally polymerizing the curable composition.

Specifically, the following compounds can be used as the thermal radical polymerization initiator. Examples of the thermal radical polymerization initiator include 1,1-di(t-hexylperoxy)cyclohexane, 1,1-di(t-butylperoxy)cyclohexane, 2,2-di(4,4-di-(t-butylperoxy)cyclohexyl)propane, t-hexylperoxyisopropyl monocarbonate, t-butylperoxy-3,5,5-trimethylhexanoate, t-butylperoxy laurate, dicumyl peroxide, di-t-butyl peroxide, t-butylperoxy-2-ethylhexanoate, t-hexylperoxy-2-ethylhexanoate, cumene hydroperoxide, t-butyl hydroperoxide, and 2,3-dimethyl-2,3-diphenylbutane.

Above all, in the present invention, it is preferable to use a hydroperoxide-based thermal radical polymerization initiator having a hydroperoxide group in the molecule as the thermal radical polymerization initiator, and it is more preferable to use at least one hydroperoxide-based thermal radical polymerization initiator having a hydroperoxide group in the molecule and at least one non-hydroperoxide-based thermal radical polymerization initiator having no hydroperoxide group in the molecule.

In the present invention, PERBUTYL O (t-butylperoxy-2-ethylhexanoate, manufactured by NOF Corporation) can be preferably used as the non-hydroperoxide-based thermal radical polymerization initiator, and PERCUMYL H-80 (cumene hydroperoxide, manufactured by NOF Corporation) can be preferably used as the hydroperoxide-based thermal radical polymerization initiator.

The reason why use of the hydroperoxide-based thermal radical polymerization initiator having a hydroperoxide group in the molecule is preferred as the thermal radical polymerization initiator is that the hydroperoxide-based thermal radical polymerization initiator has an effect of promoting a chain transfer during polymerization of a non-conjugated vinylidene group-containing compound monomer by which the three-dimensional structure can be more favorably controlled and the semi-cured product can be given good deformability. In a case where such a hydroperoxide-based thermal radical polymerization initiator is used, the temperature at which thermal radical polymerization is initiated is generally high, and therefore in such a case, it is more preferable that the hydroperoxide-based thermal radical polymerization initiator is used along with a non-hydroperoxide-based thermal radical polymerization initiator having a low thermal polymerization initiation temperature.

The content of the thermal radical polymerization initiator is preferably 0.01% to 10% by mass, more preferably 0.05% to 5.0% by mass, and still more preferably 0.05% to 2.0% by mass, with respect to the total mass of the curable composition.

The curable composition preferably contains both a photoradical polymerization initiator and a thermal radical polymerization initiator described above, and in this case, the total content of a photoradical polymerization initiator and a thermal radical polymerization initiator is preferably 0.01% to 10% by mass, more preferably 0.05% to 5.0% by mass, and still more preferably 0.05% to 3.0% by mass, with respect to the total mass of the curable composition.

(Thickener)

The curable composition according to the embodiment of the present invention may further contain a thickener if necessary. The thickener is preferably added only in a case where it is necessary to adjust the viscosity of the curable composition within a desired range.

The thickener is preferably a polymer, and such a polymer can also be referred to as a thickening polymer. The thickening polymer may be a homopolymer or a copolymer. Above all, the thickening polymer is preferably a copolymer, and more preferably a copolymer containing a monomer unit having a polymerizable group in the side chain and a monomer unit having an aryl group in the side chain.

Specific examples of the thickening polymer preferably used in the present invention are listed below, but the polymer is not limited to the following structures.

In the following structural formulae, Ra and Rb each independently represent a hydrogen atom or an alkyl group. Note that a plurality of Ra's in one polymer may be the same or different. n represents an integer of 0 to 10, preferably 0 to 2, and more preferably 0 or 1.

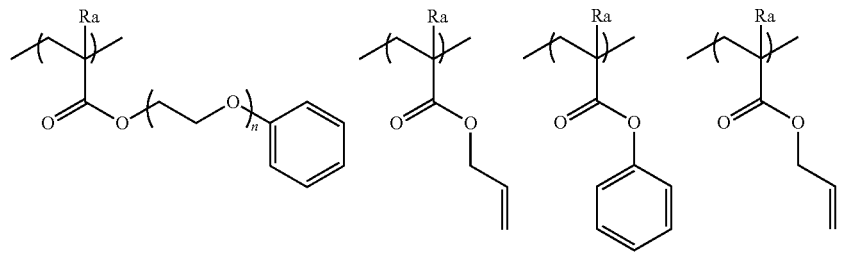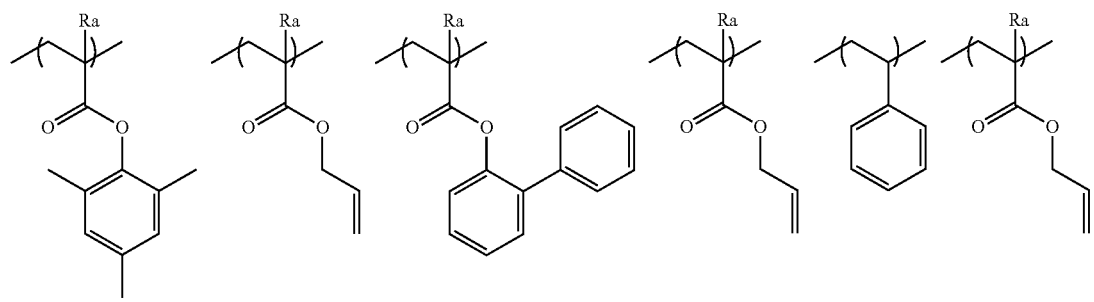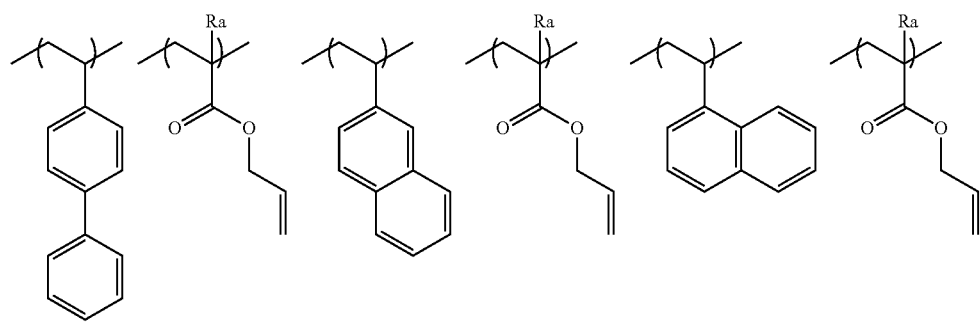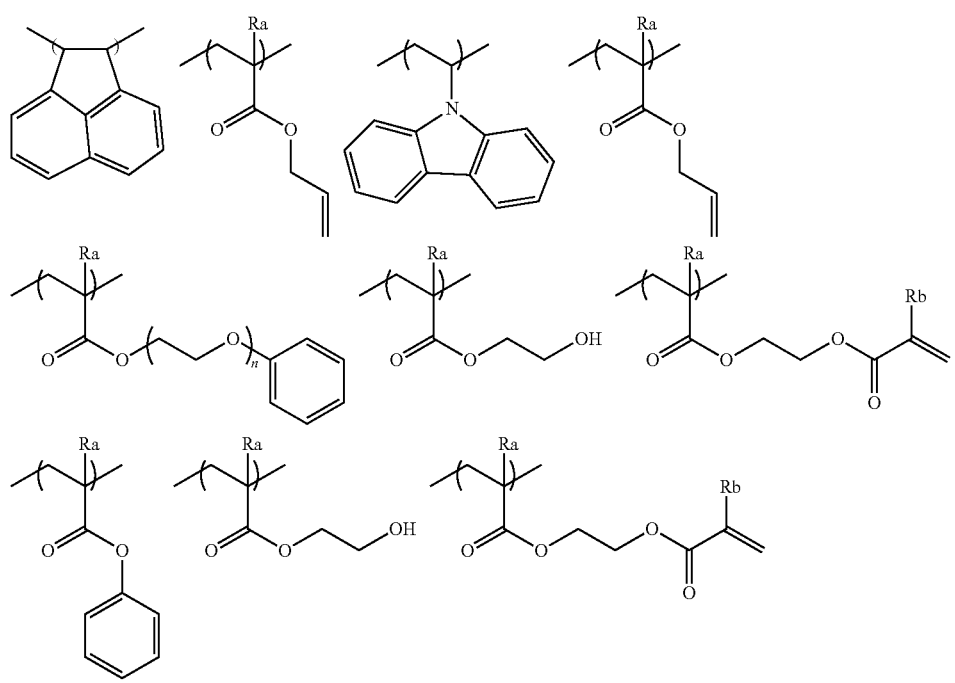

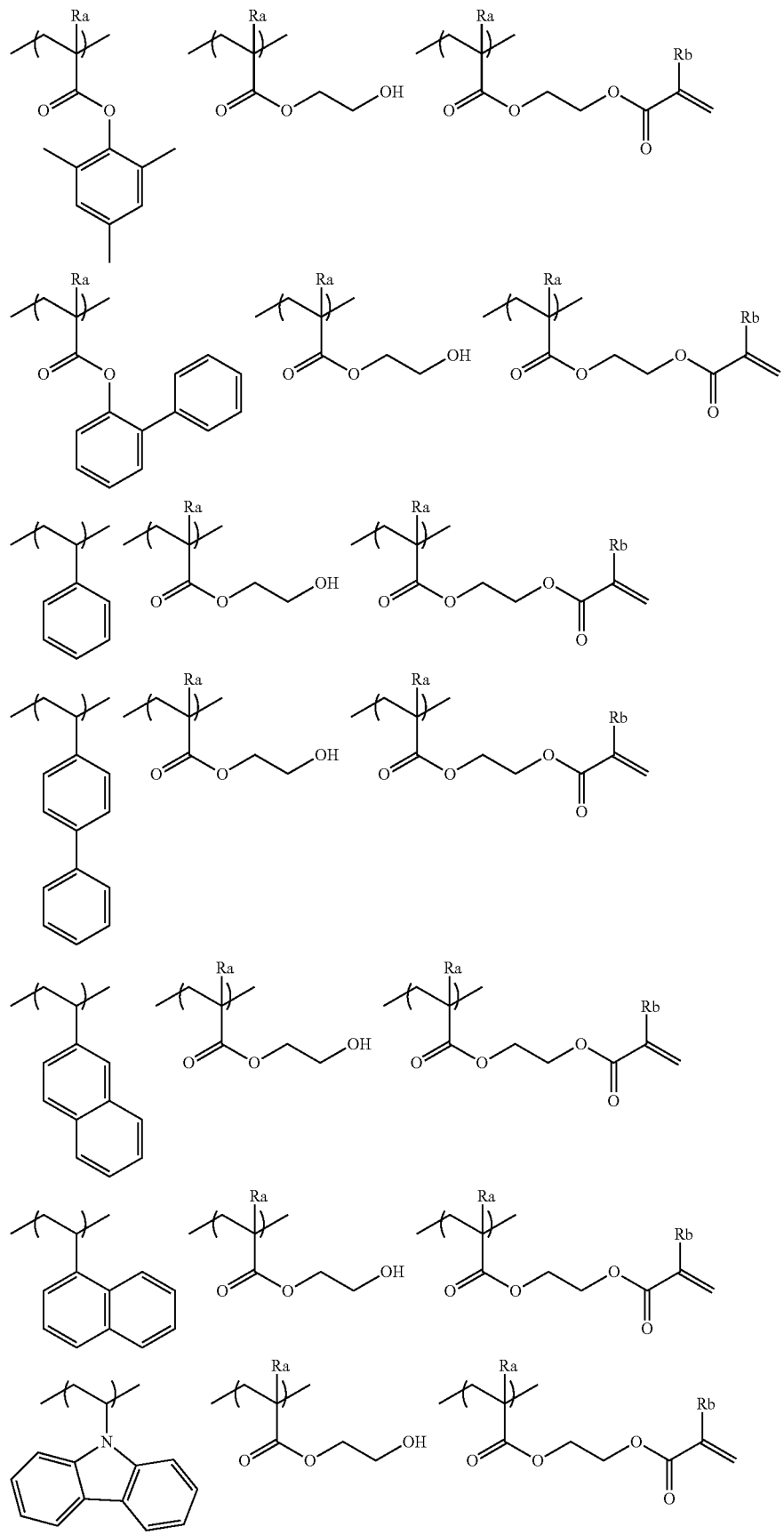

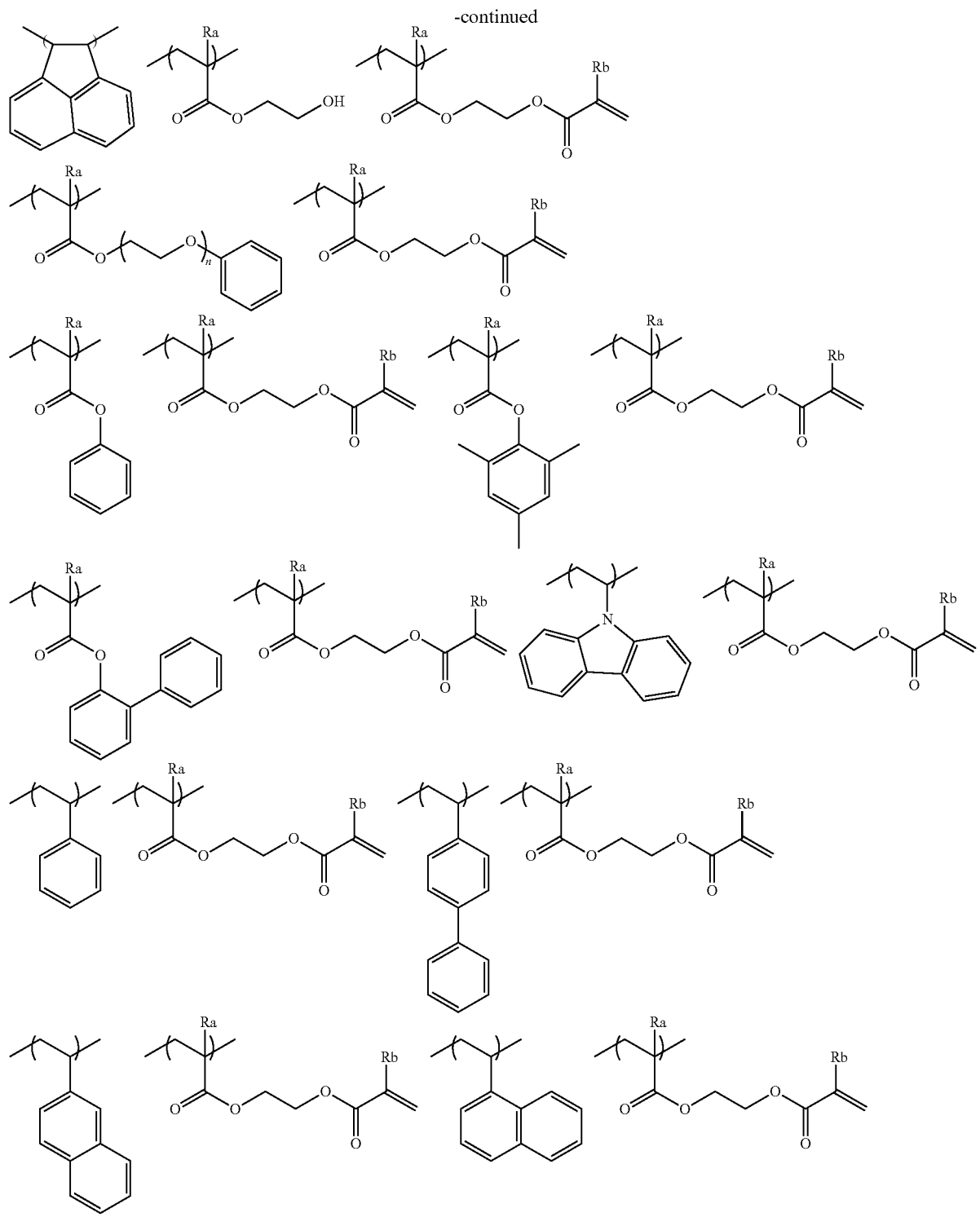

The molecular weight of the thickening polymer is preferably 1,000 to 10,000,000, more preferably 5,000 to 300,000, and still more preferably 10,000 to 200,000. The glass transition temperature of the thickening polymer is preferably 50° C. to 400° C., more preferably 70° C. to 350° C., and still more preferably 100° C. to 300° C.

The content of the thickening polymer is preferably 20% by mass or less, more preferably 15% by mass or less, still more preferably 10% by mass or less, even more preferably 7.5% by mass or less, and particularly preferably 5% by mass or less, with respect to the total mass of the curable composition. Further, an aspect in which the thickening polymer is not added is also preferable. In the present invention, it is possible to mold a cured product from the curable composition without decreasing the amount of the thickening polymer to be added or without adding the thickening polymer at all. In the present invention, by setting the content of the thickening polymer within the above range, the content of the compound represented by General Formula (1) can be increased, so that the refractive index of the cured product can be more effectively increased.

(Other Additives)

In the present invention, unless contrary to the gist of the present invention, the curable composition may contain additives such as a polymer, a monomer, a dispersant, a plasticizer, a thermal stabilizer, or a mold release agent other than those described above.

(Method for Producing Semi-Cured Product)

The semi-cured product can be produced by semi-curing the curable composition according to the embodiment of the present invention. The method for producing a semi-cured product includes a step of semi-curing the curable composition according to the embodiment of the present invention. The step of semi-curing may be a step of photoirradiation or heating.

In the step of semi-curing, the curable composition according to the embodiment of the present invention is preferably subjected to at least one of photoirradiation or heating to form a semi-cured product having a complex viscosity of $10^5$ to $10^8$ mPa·s at 25° C. and a frequency of 10 Hz.

As used herein, the term "semi-cured product" in the present specification refers to a product obtained by polymerizing a curable composition, which is not completely solid and has fluidity to some extent. A polymer of a curable composition in such a state that its complex viscosity at 25° C. and at a frequency of 10 Hz is $10^5$ to $10^8$ mPa·s is a semi-cured product. That is, those of which the upper limit value of the complex viscosity at 25° C. and at a frequency of 10 Hz is less than $1.0 \times 10^9$ mPa·s are considered to fall within a range of semi-cured products. On the other hand, the term "cured product" refers to a product produced by polymerizing a curable composition and is in a state of being completely solid.

Hereinafter, the method for producing a semi-cured product and the method for producing a cured product will be specifically described. The method for producing a cured product includes the method for producing a semi-cured product, and therefore preferred embodiments of the production method common to both the two are described in the method for producing a semi-cured product.

<Semi-Curing Step>

The method for producing a semi-cured product preferably includes a step of photoirradiating and/or heating the curable composition to obtain a semi-cured product having a complex viscosity of $10^5$ to $10^8$ mPa·s at 25° C. and at a frequency of 10 Hz.

In the method for producing a semi-cured product, the curable composition may be directly placed in a molding mold to be used in thermal polymerization, before photoirradiation and/or heating of the composition, or alternatively, the curable composition may be placed in a mold different from the molding mold for thermal polymerization to produce a semi-cured product, and then transferred to the molding mold to be used in thermal polymerization.

In a case where a mold different from the molding mold for thermal polymerization is used, preferred is the use of a so-called mold for preforming. The mold for preforming may be formed of metal, or may be formed of glass or resin. In consideration of using the mold repeatedly in a mass-production line, the mold for preforming is preferably formed of metal or glass. In a case where the semi-cured product is used for lenses, it is preferred that at least one side of the mold for preforming has a shape that is the same or similar to the shape of the molding mold for thermal polymerization, and it is more preferred that both sides of the mold for preforming have a shape that is the same or similar to the shape of the molding mold for thermal polymerization.

The photoirradiation in the method for producing a semi-cured product is carried out so that the complex viscosity of the semi-cured product at 25° C. and at a frequency of 10 Hz after photoirradiation is preferably $10^5$ to $10^8$ mPa·s, more preferably $10^5$ to $10^{7.5}$ mPa·s, and particularly preferably $10^{5.5}$ to $10^{7.5}$ mPa·s.

The light used in the photoirradiation is preferably ultraviolet light or visible light and more preferably ultraviolet light. For example, a metal halide lamp, a low pressure mercury lamp, a high pressure mercury lamp, an ultrahigh pressure mercury lamp, a germicidal lamp, a xenon lamp, or a light emitting diode (LED) light source lamp is suitably used. The atmosphere during photoirradiation is preferably air or an inert gas purged atmosphere and is more preferably an atmosphere purged with nitrogen until an oxygen concentration becomes 1% or less.

In a case of providing a semi-curing step by heating in the method for producing a semi-cured product, the semi-curing by heating is carried out so that the complex viscosity of the semi-cured product at 25° C. and at a frequency of 10 Hz after heating is preferably $10^5$ to $10^8$ mPa·s, more preferably $10^5$ to $10^{7.5}$ mPa·s, and particularly preferably $10^{5.5}$ to $10^{7.5}$ mPa·s.

(Semi-Cured Product)

The present invention may relate to a semi-cured product produced by the above-described method. Such a semi-cured product may be preferably used for a method for producing a cured product to be described later. Here, the preferred range of the complex viscosity of the semi-cured product is the same as the preferred range of the complex viscosity of the semi-cured product in the above-described method for producing a semi-cured product.

The semi-cured product may not contain the photoradical polymerization initiator at all after the photoirradiation step, since the initiator is completely consumed in the step, or the photoradical polymerization initiator may remain in the semi-cured product.

In addition, the glass transition temperature of the semi-cured product is preferably −150° C. to 0° C., more preferably −50° C. to 0° C., and particularly preferably −20° C. to 0° C.

(Method for Producing Cured Product)

The method for producing a cured product preferably includes a thermal polymerization step of putting the semi-cured product in a molding mold for pressure deformation therein, and heating it therein for thermal polymerization to obtain a cured product or a photopolymerizing step of photoirradiating the semi-cured product to obtain a cured product.

The method for producing a cured product preferably includes a step of subjecting the curable composition according to the embodiment of the present invention to at least one of photoirradiation or heating to obtain a semi-cured product having a complex viscosity of $10^5$ to $10^8$ mPa·s at 25° C. and at a frequency of 10 Hz, and a polymerization step of putting the semi-cured product in a molding mold for pressure deformation therein and then subjecting the semi-cured product to at least one of photoirradiation or heating to obtain a cured product. The photoirradiation conditions and the heating conditions in the production step of a cured product are the same as those in the semi-curing step described above.

In a case where the production step of a cured product is a thermal polymerization step, the molding mold used in the polymerization step is also referred to as a thermoforming mold. In general, the thermoforming mold is composed of two molding mold parts and is preferably designed so that contents can be heated under pressure in the combination of the two molding mold parts. In the method for producing a cured product, a metallic mold is more preferably used as the molding mold in the thermal polymerization step to obtain a cured product. The thermoforming mold of the type for use herein is described, for example, in JP2009-126011A.

In the method for producing a cured product, first, the semi-cured product produced according to the semi-cured product production method is put into a molding mold. The semi-cured product after photoirradiation and/or heating is directly set in a thermoforming mold and is photoirradiated and/or heated therein, or is set in a mold different from a thermoforming mold and is photoirradiated and/or heated therein, as described in the section of Method for producing semi-cured product. In a case where the semi-cured product after photoirradiation is directly set in a thermoforming mold and is photoirradiated and/or heated therein, the operation of transferring the semi-cured product into a thermoforming mold is unnecessary. On the other hand, in a case where the semi-cured product after photoirradiation and/or heating is set in a mold different from a thermoforming mold and is photoirradiated and/or heated therein, it is preferred to include a step of transferring the semi-cured product into a thermoforming mold. For the method of transferring the semi-cured product after photoirradiation and/or heating into a thermoforming mold, for example, an air tweezer equipped with a syringe, a vacuum pad, and a vacuum generator may be used. The semi-cured product has a complex viscosity falling within a specific range, and therefore can be readily transferred into a thermoforming mold by the use of such an air tweezer.

According to the method for producing a cured product, the semi-cured product put in a molding mold is deformed under pressure and heated for thermal polymerization to obtain a cured product. Here, pressure deforming and heating may be carried out simultaneously, or heating may be carried out after pressure deforming, or pressure deforming may be carried out after heating. Above all, preferably, pressure deforming and heating are carried out simultaneously. Also preferably, after simultaneous pressure deforming and heating, the product may be further heated at a higher temperature after the pressure applied thereto has become stable.

The pressure for the pressure deforming is preferably 0.098 MPa to 9.8 MPa, more preferably 0.294 MPa to 4.9 MPa, and particularly preferably 0.294 MPa to 2.94 MPa. In a case where the heating is carried out simultaneously with pressure deforming, the heating temperature is preferably 80° C. to 300° C., more preferably 120° C. to 300° C., and particularly preferably 150° C. to 280° C. On the other hand, in a case where the product is further heated at a higher temperature after the pressure applied thereto has become stable, the heating temperature is preferably 80° C. to 300° C., more preferably 120° C. to 300° C., and particularly preferably 150° C. to 280° C. The time of thermal polymerization is preferably 30 to 1,000 seconds, more preferably 30 to 500 seconds, and particularly preferably 60 to 300 seconds. The atmosphere during thermal polymerization is preferably air or an inert gas purged atmosphere and more preferably an atmosphere purged with nitrogen until an oxygen concentration becomes 1% or less.

(Cured Product)

The present invention also relates to a cured product of a curable composition. The cured product is formed by curing the above-mentioned semi-cured component. The cured product according to the embodiment of the present invention is preferably a cured product produced by the above-mentioned method for producing a cured product.

(Refractive Index)

The cured product according to the embodiment of the present invention preferably has a high refractive index from the viewpoint of using it for optical members, especially for lenses. The refractive index nD at a wavelength of 589 nm of the cured product according to the embodiment of the present invention is preferably 1.58 or more, more preferably 1.60 or more, and still more preferably 1.61 or more. The refractive index of the cured product at 589 nm can be measured using an Abbe meter (manufactured by Atago Co., Ltd.).

(Size)

The maximum thickness of the cured product according to the embodiment of the present invention is preferably 0.1 to 10 mm. The maximum thickness is more preferably 0.1 to 5 mm and particularly preferably 0.15 to 3 mm. The maximum diameter of the cured product according to the embodiment of the present invention is preferably 1 to 1,000 mm. The maximum diameter is more preferably 2 to 200 mm and particularly preferably 2.5 to 100 mm. The cured product having such a size as above is especially useful for optical members having a high refractive index. In general, it is not easy to produce such a thick molded body according to a solution casting method since the solvent is difficult to remove, or that is, molding the molded body is not easy. However, the use of the curable composition according to the embodiment of the present invention makes it easy to mold such a thick molded body and provides high handleability, whereby a cured product of high quality can be obtained.

(Optical Members)

The present invention also relates to an optical member including the above-mentioned cured product. Since the cured product according to the embodiment of the present invention is a molded body having excellent optical properties, it is preferably used as an optical member. The type of the optical member according to the embodiment of the present invention is not particularly limited. In particular, the cured product according to the embodiment of the present invention is suitably used for optical members that utilize the excellent optical properties of curable compositions, especially for light-transmissive optical members (so-called passive optical members). Examples of optically-functional devices equipped with such optical members include various types of display devices (a liquid crystal display, a plasma display, and the like), various types of projector devices (an overhead projector (OHP), a liquid crystal projector, and the like), optical fiber communication systems (a light waveguide, a light amplifier, and the like), and image-taking devices such as a camera and a video.

Examples of the passive optical members for use in optically-functional devices include lenses, prisms, prism sheets, panels (plate-like molded bodies), films, optical waveguides (film-like optical waveguide, a fiber-like optical waveguide, and the like), optical discs, and LED sealants. If desired, the passive optical members may be provided with an optional coating layer, such as a protective layer for preventing mechanical damage of the coating surface by friction or abrasion, a light-absorbing layer for absorbing the light having an undesirable wavelength to cause degradation of inorganic particles, substrates and others, a blocking layer for suppressing or preventing permeation of reactive small molecules such as moisture or oxygen gas, an antiglare layer, an antireflection layer, a layer of low refractive index, or the like, as well as any additional functional layer. Specific examples of the optional coating layer include a transparent conductive film or gas barrier film formed of an inorganic oxide coating layer, and a gas barrier film or hard coating film formed of an organic coating layer. The coating method for these layers may be any known coating method such as a vacuum deposition method, a chemical vapor deposition (CVD) method, a sputtering method, a dip coating method, or a spin coating method.

APPLICATION EXAMPLES

The optical member using the cured product according to the embodiment of the present invention is especially preferable for a lens substrate. The lens substrate produced using the curable composition according to the embodiment of the present invention has a low Abbe's number and preferably has high refractivity, high light transmittance and light-weightness and is excellent in optical properties. By suitably adjusting the type of monomer constituting the curable composition, it is possible to control the refractive index of the lens substrate in any desired manner.

In addition, in the present specification, the "lens substrate" refers to a single member capable of exhibiting a lens function. On and around the surface of the lens substrate, any film and member may be provided depending on the use environment and applications of lenses. For example, a protective film, an antireflection film, a hard coating film, or the like may be formed on the surface of the lens substrate. Further, it can be a compound lens in which a glass lens substrate or a plastic lens substrate is laminated. It is also possible to make the periphery of the lens substrate intrude and be fixed in a substrate holding frame. However, those films and frames are additional members to the lens substrate and therefore differ from the lens substrate itself referred to in the present specification.

In a case of using the lens substrate for lenses, the lens substrate itself may be used as a lens by itself, or additional films or frames or additional lens substrates may be added thereto for use as a lens, as mentioned above. The type and the shape of the lens using the lens substrate are not particularly limited.

The lens substrate has a low Abbe's number and is therefore preferably used for an achromatic lens, and the achromatic lens is used, for example, for lenses for imaging devices such as mobile phones or digital cameras; lenses for movie devices such as TV or video cameras; and lenses for in-vehicle devices or endoscope lenses.

EXAMPLES

Hereinafter, the features of the present invention will be more specifically described with reference to Examples and Comparative Examples. In the following Examples, the materials to be used, amounts and ratios thereof, the details of the treatment and the treatment procedures, and the like may be suitably modified or changed without departing from the scope of the present invention. Accordingly, the scope of the present invention should not be limitedly interpreted by the following specific Examples.

(Synthesis of Compound (A))

132 mL of triethylamine and 650 mL of butyl acetate were added to 100 g of 2-hydroxyethyl acrylate, followed by stirring. While maintaining the reaction solution at 5° C., 70 mL of methanesulfonic acid chloride was added dropwise over 1 hour. After stirring for 1 hour, 500 mL of water was added to the reaction solution, followed by stirring, and the operation of removing the water layer was repeated three times. Subsequently, 30 mg of dibutylhydroxytoluene was added and then the pressure of the reaction system was reduced to distill the butyl acetate to obtain 160 g of Compound (A).

(Synthesis of Compound (B))

Compound (B) was synthesized in the same manner as in the synthesis of Compound (A), except that 2-hydroxyethyl acrylate was replaced by ethylene glycol monoallyl ether.

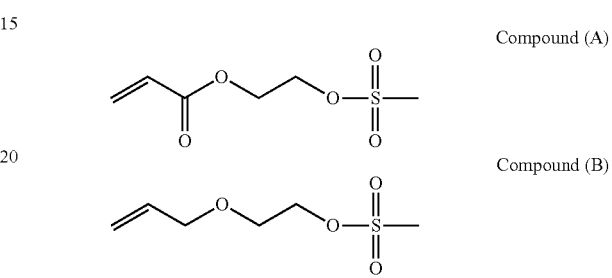

Compound (A)

Compound (B)

(Synthesis of Precursor (1))

Precursor (1) was synthesized by the method described in CHIRALITY, 12 (2000), p. 510.

(Synthesis of Precursor (2))

Precursor (2) was synthesized in the same manner as in the synthesis of Precursor (1), except that 6-quinolinol was replaced by 7-quinolinol.

Precursor (1)

Precursor (2)

(Synthesis of Compound (2))

50 mL of tetrahydrofuran, 0.05 mL of nitrobenzene, 13.8 g of potassium carbonate, and 0.8 g of tetrabutylammonium bromide (TBAB) were added to 7.2 g of Precursor (1), followed by stirring. 15 g of Compound (A) was added to the resulting reaction solution which was then reacted for 5 hours while being kept at 80° C. Thereafter, 100 mL of toluene was added thereto, followed by stirring. 100 mL of water was added to this reaction solution which was then stirred while being kept at 60° C., and the operation of removing the water layer was repeated three times. The residue was purified by silica gel column chromatography to obtain 9.2 g of Compound (2). The $^1$H-Nuclear Magnetic Resonance (NMR) data of Compound (2) was as follows.

$^1$H-NMR (300 MHz, DMSO-d6): δ4.05-4.15 ppm (m, 4H), 4.25-4.35 ppm (m, 4H), 5.70-5.85 ppm (m, 4H), 5.95-6.05 ppm (m, 2H), 7.20-7.35 ppm (m, 4H), 7.85 ppm (d, 2H), 8.15 ppm (d, 2H), 8.75 ppm (dd, 2H)

(Synthesis of Compound (1))

Compound (1) was synthesized in the same manner as in the synthesis of Compound (2), except that Compound (A) was replaced by Compound (B). The $^1$H-NMR data of Compound (1) was as follows.

$^1$H-NMR (300 MHz, DMSO-d6): δ3.95-4.05 ppm (m, 4H), δ4.10-4.20 ppm (m, 4H), 4.25-4.35 ppm (m, 4H), 5.20-5.30 ppm (m, 4H), 5.85-5.95 ppm (m, 2H), 7.20-7.35 ppm (m, 4H), 7.85 ppm (d, 2H), 8.15 ppm (d, 2H), 8.78 ppm (dd, 2H)

(Synthesis of Compound (8))

Compound (8) was synthesized in the same manner as in the synthesis of Compound (2), except that Compound (A) was replaced by (2R)-(−)-glycidyl p-toluenesulfonate (manufactured by Tokyo Chemical Industry Co., Ltd.). The $^1$H-NMR data of Compound (8) was as follows.

$^1$H-NMR (300 MHz, DMSO-d6): δ2.63-2.67 ppm (dd, 2H), 2.83 ppm (t, 2H), 3.25-3.30 ppm (m, 2H), 3.75-3.80 ppm (m, 2H) 4.20-4.25 ppm (dd, 2H), 7.20-7.35 ppm (m, 4H), 7.85 ppm (d, 2H), 8.15 ppm (d, 2H), 8.78 ppm (dd, 2H)

(Synthesis of Compound (12))

Compound (12) was synthesized in the same manner as in the synthesis of Compound (2), except that Precursor (1) was replaced by Precursor (2). The $^1$H-NMR data of Compound (12) was as follows.

$^1$H-NMR (300 MHz, DMSO-d6): δ4.05-4.15 ppm (m, 4H), 4.25-4.35 ppm (m, 4H), 5.70-5.85 ppm (m, 4H), 5.95-6.05 ppm (m, 2H), 7.18 ppm (dd, 2H), 7.50 ppm (d, 2H) 7.90 ppm (d, 2H), 8.20 ppm (d, 2H), 8.75 ppm (dd, 2H)

(Synthesis of Comparative Compound (1))

Comparative Compound (1) was synthesized with reference to paragraph [0070] of JP4803331B.

Comparative Compound (1)

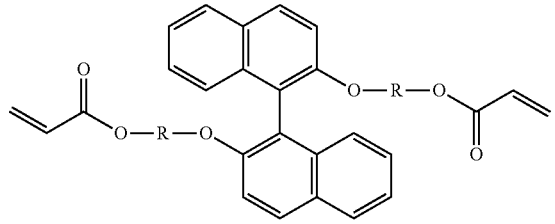

R represents an alkylene group with group/propylene group = 90/10 (molar ratio).

Examples 1 to 5 and Comparative Examples 1 and 2

The following components were added to the above compound so as to have the composition described in the following table, and the mixture was stirred to make it homogeneous to prepare a curable composition.

<(Meth)Acrylate Monomer>

The following compound was used as the (meth)acrylate monomer.

Monomer 1: trade name VISCOAT #192PEA, manufactured by Osaka Organic Chemical Industry Ltd.

Monomer 1

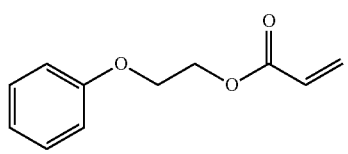

<Thickener>

A thickening polymer (E-1) was synthesized with reference to paragraph [0102] of JP5898551B. The thickening polymer (E-1) had a weight-average molecular weight of 38,700 in terms of standard polystyrene as measured by a gel permeation chromatography (GPC) method, and a dispersivity (Mw/Mn) of 3.8.

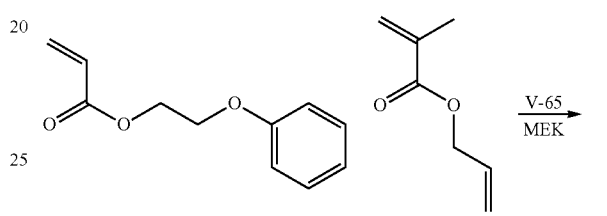

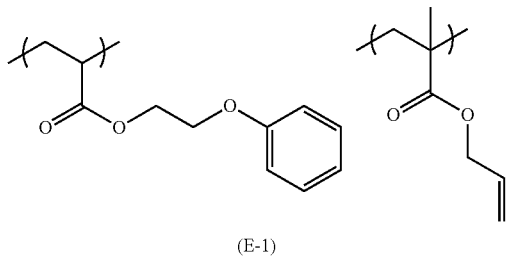

(E-1)

<Non-Conjugated Vinylidene Group-Containing Compound>

The following compound (β-caryophyllene, manufactured by Inoue Perfumery Mfg. Co., Ltd.) was used as the non-conjugated vinylidene group-containing compound. There is no particular restriction on the optical isomers thereof.

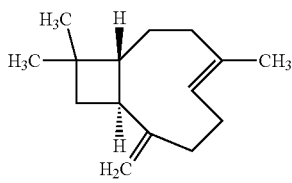

β-caryophyllene

<Photoradical Polymerization Initiator>

The following compound (IRGACURE 819, manufactured by BASF Corporation) was used as the photoradical polymerization initiator.

Irgacure 819

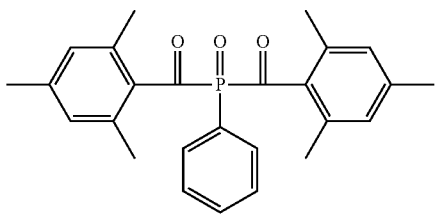

<Thermal Radical Polymerization Initiator>
The following compounds were used as the thermal radical polymerization initiator.
PERBUTYL O: manufactured by NOF Corporation
PERCUMYL H-80: manufactured by NOF Corporation

PERBUTYL O

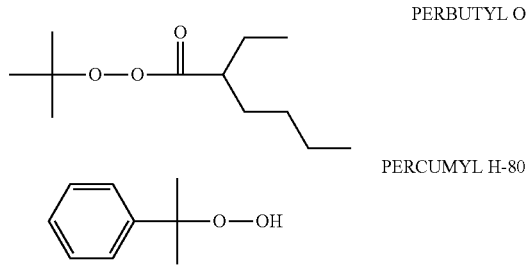

PERCUMYL H-80

(Evaluation)
<Properties of Curable Composition (Viscosity of Curable Composition at 25° C., 10 Hz)>
With respect to the curable compositions obtained in Examples and Comparative Examples, a dynamic complex viscosity value at 25° C. and 10 Hz was measured using RHEOSTRESS RS600 (manufactured by HAAKE GmbH) and it was taken as the liquid viscosity of the curable composition.

<Evaluation of Mold Resin Clearance Leakage>
A ceiling mold of a thermoforming mold for forming a lens having a diameter of 4.0 mm and including an upper mold (ceiling mold), a trunk mold, and a lower mold (bottom mold) was removed and 10 mg of the curable composition was injected. The injected curable composition was irradiated with ultraviolet light of 15 mW/cm² for 20 seconds using an Execure 3000 (manufactured by Hoya Corporation) to produce a semi-cured product. Subsequently, the semi-cured product was placed in the ceiling mold, and the thermoforming mold was heated to 80° C. Thereafter, the temperature was raised to 200° C. while applying a pressure of 2.94 MPa (30 kgf/cm²) to the semi-cured product, and then the temperature was cooled to room temperature.

In the step of injecting the curable composition into the thermoforming mold and cooling the composition to room temperature, the weight of the curable composition (resin) leaked to the clearance of the thermoforming mold (the gap formed between the trunk mold and the upper/lower molds) was measured and evaluated according to the following standards. B rating or higher was regarded as acceptable level.

A: Leakage of the curable composition (resin) was less than 0.1 mg.
B: Leakage of the curable composition (resin) was 0.1 mg or more and less than 0.2 mg.
C: Leakage of the curable composition (resin) was 0.2 mg or more.

<Refractive Index of Cured Product>
Each of the curable compositions obtained in Examples and Comparative Examples was injected into a transparent glass mold having a diameter of 10 mm and a thickness of 1 mm and irradiated with ultraviolet light of 15 mW/cm² for 20 seconds using an Execure 3000 (manufactured by Hoya Corporation) to obtain a semi-cured product. Subsequently, the obtained semi-cured product was taken out of the transparent glass mold and heated at 200° C. for 5 minutes using a hot plate to obtain a cured product. The refractive index of the obtained cured product at 589 nm was measured using an Abbe meter (manufactured by Atago Co., Ltd.) and it was taken as the refractive index of the cured product. A refractive index of 1.58 or more at 589 nm was regarded as acceptable level.

<Production of Compound Lens>
200 mg of each of the curable compositions obtained in Examples and Comparative Examples was injected into a metallic molding mold (the surface in contact with the curable composition is a curved surface for forming a lens). Subsequently, a transparent glass lens (glass material BK-7, refractive index: 1.509) was placed so as to cover all the surfaces of the curable composition not in contact with the metallic molding mold, so that all the surfaces of the curable composition were filled so as to be in contact with the metallic molding mold or glass lens (so as not to incorporate bubbles). After this state, a semi-cured product was prepared by irradiating ultraviolet light of 15 mW/cm² for 20 seconds from above the glass lens using an Execure 3000 (manufactured by Hoya Corporation). Then, while maintaining the state sandwiched between the metallic molding mold and the glass lens, the temperature was raised to 200° C. while applying a pressure of 0.196 MPa (2 kgf/cm²) to the semi-cured product, and then the temperature was cooled to room temperature. Thereafter, the compound lens in which the cured product (height: 200 μm) of the curable composition and the glass lenses were laminated was taken out from the metallic molding mold. In order to use for the following evaluation, the above step was repeated ten times to produce ten compound lenses.

<Evaluation of Compound Lens>
(Transferability)
The appearance of each compound lens produced as described above was evaluated using a FormTalysurf SSC (manufactured by Taylor-Hobson Ltd.) and a digital microscope (trade name: VHX-1000, manufactured by Keyence Corporation).

Those with fine irregularities (wrinkles) on the surface of the flange portion of the lens or cracks in the lens were regarded as defective products, and those without fine irregularities or cracks were regarded as non-defective products. Ten compound lenses were evaluated, and the percentage of non-defective products among them was evaluated as a non-defective rate and evaluated according to the following standards.

A: The non-defective rate was 80% or more.
B: The non-defective rate was 50% or more and less than 80%.
C: The non-defective rate was less than 50%.

TABLE 2

|  |  | Example 1 | Example 2 | Example 3 | Example 4 | Example 5 | Comparative Example 1 | Comparative Example 2 |
|---|---|---|---|---|---|---|---|---|
| Compound represented by General Formula (1) | Compound (1) | 65.6 | 61.6 |  |  |  |  |  |
|  | Compound (2) |  |  | 65.6 |  |  |  |  |
|  | Compound (8) |  |  |  | 65.6 |  |  |  |
|  | Compound (12) |  |  |  |  | 65.6 |  |  |
| Comparative Compound | Comparative Compound (1) |  |  |  |  |  | 65.6 | 48.1 |
| (Meth)acrylate monomer | Monomer 1 | 28.1 | 27.1 | 28.1 | 28.1 | 28.1 | 28.1 | 20.6 |
| Thickener | Thickening polymer (E-1) | 0.0 | 5.0 | 0.0 | 0.0 | 0.0 | 0.0 | 25.0 |
| Non-conjugated vinylidene group-containing compound | β-caryophyllene | 4.5 | 4.5 | 4.5 | 4.5 | 4.5 | 4.5 | 4.5 |
| Photoradical polymerization initiator | IRGACURE 819 | 0.1 | 0.1 | 0.1 | 0.1 | 0.1 | 0.1 | 0.1 |
| Thermal radical polymerization initiator | PERBUTYL O | 1.0 | 1.0 | 1.0 | 1.0 | 1.0 | 1.0 | 1.0 |
|  | PERCUMYL H-80 | 0.7 | 0.7 | 0.7 | 0.7 | 0.7 | 0.7 | 0.7 |
| Viscosity of curable composition (mPa · s) |  | 4500 | 5300 | 5400 | 5100 | 5200 | 425 | 4400 |
| Evaluation of mold resin clearance leakage |  | B | A | A | A | A | C | B |
| Evaluation of transferability of compound lens |  | A | A | A | B | A | C | B |
| Refractive index of cured product |  | 1.62 | 1.61 | 1.63 | 1.63 | 1.61 | 1.60 | 1.57 |

From Table 2, the curable compositions of Examples had a viscosity suitable for molding and exhibited an excellent molding stability. In addition, the cured products molded from the curable compositions of Examples had a high refractive index.

In Examples 1 and 3 to 5, molding of a cured product could be carried out without adding a thickening polymer. Also in Example 2, molding of a cured product could be carried out by adding a small amount of a thickening polymer. In a case where the amount of the thickening polymer added was small or in a case where the thickening polymer was not added, the refractive index of the cured product could be increased.

Further, in a case where the partial structure A of the compound represented by General Formula (1) is a compound having a (meth)acryloyl group, the transferability of the compound lens was further improved.

What is claimed is:

1. A curable composition comprising:
a compound represented by General Formula (1):

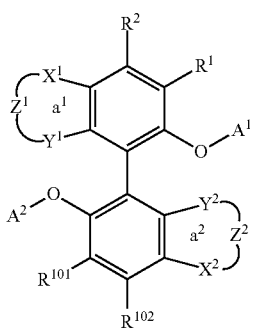

General Formula (1)

in General Formula (1), $X^1$, $X^2$, $Y^1$, and $Y^2$ each independently represent a nitrogen atom, or a carbon atom to which a hydrogen atom or a substituent may be bonded;
$Z^1$ is an atom or atomic group forming a 5- to 7-membered ring $a^1$ together with $X^1$—C=C—$Y^1$ and contains at least one selected from the group consisting of an oxygen atom, a sulfur atom, a nitrogen atom, and a carbon atom;
$Z^2$ is an atom or atomic group forming a 5- to 7-membered ring $a^2$ together with $X^2$—C=C—$Y^2$ and contains at least one selected from the group consisting of an oxygen atom, a sulfur atom, a nitrogen atom, and a carbon atom;
the ring $a^1$ has an oxygen atom, a sulfur atom, or a nitrogen atom as a ring skeleton atom and when the ring $a^1$ has two adjacent carbon atoms, the ring $a^1$ may have a fused ring having the two adjacent carbon atoms as ring skeleton atoms;
the ring $a^2$ has an oxygen atom, a sulfur atom, or a nitrogen atom as a ring skeleton atom, and when the ring $a^2$ has two adjacent carbon atoms, the ring $a^2$ may have a fused ring having the two adjacent carbon atoms as ring skeleton atoms;
$A^1$ and $A^2$ each independently represent a substituent containing at least one crosslinkable group selected from the group consisting of a vinyl group, an epoxy group, and a (meth)acryloyl group; and
$R^1$, $R^2$, $R^{101}$, and $R^{102}$ each independently represent a hydrogen atom, a halogen atom, a hydrocarbon group having 1 to 10 carbon atoms, or an alkoxy group having 1 to 10 carbon atoms.

2. The curable composition according to claim 1, wherein $A^1$ and $A^2$ each independently represent a group represented by General Formula (2):

General Formula (2)

in General Formula (2), Alkylene represents an alkylene group having 2 to 6 carbon atoms, $L^1$ represents —O—, —S—, or —NH—, n1 represents an integer of 0 to 10, and P represents a hydrogen atom or a group represented by any one of General Formulae (P1) to (P3), and
in a case where n1 is 2 or more, a plurality of Alkylene's and $L^1$'s each may be different from one another;

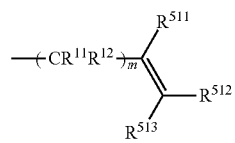

General Formula (P1)

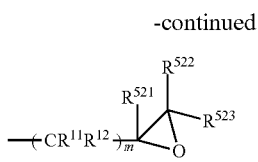
General Formula (P2)

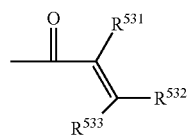
General Formula (P3)

in General Formulae (P1) to (P3), $R^{511}$, $R^{512}$, $R^{513}$, $R^{521}$, $R^{522}$, $R^{523}$, $R^{531}$, $R^{532}$, and $R^{533}$ each independently represent a hydrogen atom or an alkyl group, m represents an integer of 0 to 2, and $R^{11}$ and $R^{12}$ each independently represent a hydrogen atom or a substituent, and in a case where m is 2, a plurality of $R^{11}$'s and $R^{12}$'s each may be different from one another.

3. The curable composition according to claim 1, wherein the ring $a^1$ and the ring $a^2$ have a nitrogen atom as a ring skeleton atom.

4. The curable composition according to claim 1, wherein the compound represented by General Formula (1) is a compound represented by General Formula (3):

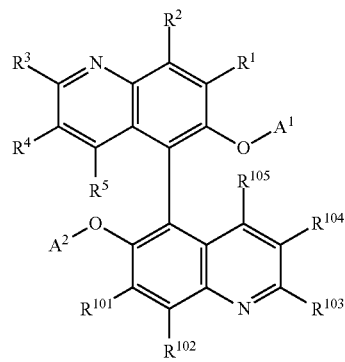
General Formula (3)

in General Formula (3), $A^1$ and $A^2$ each independently represent a substituent containing at least one cross-linkable group selected from the group consisting of a vinyl group, an epoxy group, and a (meth)acryloyl group, and $R^1$ to $R^5$ and $R^{101}$ to $R^{105}$ each independently represent a hydrogen atom, a halogen atom, a hydrocarbon group having 1 to 10 carbon atoms, or an alkoxy group having 1 to 10 carbon atoms.

5. The curable composition according to claim 1, wherein $A^1$ and $A^2$ are each independently a group represented by General Formula (4):

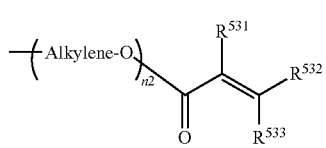
General Formula (4)

in General Formula (4), Alkylene represents an alkylene group having 2 to 6 carbon atoms, $R^{531}$, $R^{532}$ and $R^{533}$ each independently represent a hydrogen atom or an alkyl group, and n2 represents an integer of 0 to 10, and in a case where n2 is 2 or more, a plurality of Alkylene's may be different from one another.

6. The curable composition according to claim 4, wherein $A^1$ and $A^2$ are each independently a group represented by General Formula (4):

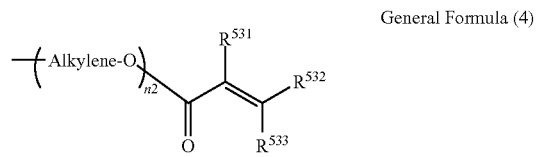
General Formula (4)

in General Formula (4), Alkylene represents an alkylene group having 2 to 6 carbon atoms, $R^{531}$, $R^{532}$ and $R^{533}$ each independently represent a hydrogen atom or an alkyl group, and n2 represents an integer of 0 to 10, and in a case where n2 is 2 or more, a plurality of Alkylene's may be different from one another.

7. The curable composition according to claim 1, further comprising:

at least one (meth)acrylate monomer having one (meth)acryloyl group in the molecule or having two or more (meth)acryloyl groups which are bonded to an aliphatic ring directly or through a divalent linking group; and at least one selected from the group consisting of a photoradical polymerization initiator and a thermal radical polymerization initiator.

8. The curable composition according to claim 1, wherein the composition has a viscosity at 25° C. of 3000 mPa·s or more and less than 20000 mPa·s.

9. A cured product of the curable composition according to claim 1.

10. An optical member comprising:
the cured product according to claim 9.

11. A lens comprising:
the cured product according to claim 9.

12. A compound represented by General Formula (1):

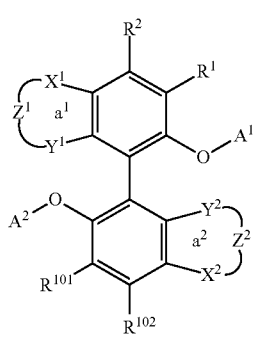
General Formula (1)

in General Formula (1), $X^1$, $X^2$, $Y^1$, and $Y^2$ each independently represent a nitrogen atom, or a carbon atom to which a hydrogen atom may be bonded;

$Z^1$ is an atom or atomic group forming a 5- to 7-membered ring $a^1$ together with $X^1$—C=C—$Y^1$ and contains at least one selected from the group consisting of an oxygen atom, a sulfur atom, a nitrogen atom, and a carbon atom;

$Z^2$ is an atom or atomic group forming a 5- to 7-membered ring $a^2$ together with $X^2$—C=C—$Y^2$ and contains at least one selected from the group consisting of an oxygen atom, a sulfur atom, a nitrogen atom, and a carbon atom;

the ring $a^1$ has an oxygen atom, a sulfur atom, or a nitrogen atom as a ring skeleton atom, and when the ring $a^1$ has two adjacent carbon atoms, the ring $a^1$ may have a fused ring having the two adjacent carbon atoms as ring skeleton atoms;

the ring $a^2$ has an oxygen atom, a sulfur atom, or a nitrogen atom as a ring skeleton atom, and when the ring $a^2$ has two adjacent carbon atoms, the ring $a^2$ may have a fused ring having the two adjacent carbon atoms as ring skeleton atoms;

$A^1$ and $A^2$ each independently represent a substituent containing at least one crosslinkable group selected from the group consisting of a vinyl group, an epoxy group, and a (meth)acryloyl group; and $R^1$, $R^2$, $R^{101}$, and $R^{102}$ each independently represent a hydrogen atom, a halogen atom, a hydrocarbon group having 1 to 10 carbon atoms, or an alkoxy group having 1 to 10 carbon atoms.

13. The compound according to claim 12, wherein $A^1$ and $A^2$ each independently represent a group represented by General Formula (2):

General Formula (2)

—(Alkylene-$L^1$)$_{n1}$-P in General Formula (2), Alkylene represents an alkylene group having 2 to 6 carbon atoms, $L^1$ represents —O—, —S—, or —NH—, n1 represents an integer of 0 to 10, and P represents a hydrogen atom or a group represented by any one of General Formulae (P1) to (P3), and in a case where n1 is 2 or more, a plurality of Alkylene's and $L^1$'s each may be different from one another;

General Formula (P1)

—(CR$^{11}$R$^{12}$)$_m$—C(R$^{511}$)=C(R$^{512}$)(R$^{513}$)

General Formula (P2)

—(CR$^{11}$R$^{12}$)$_m$—(epoxide with R$^{521}$, R$^{522}$, R$^{523}$)

General Formula (P3)

O=C—C(R$^{531}$)=C(R$^{532}$)(R$^{533}$)

in General Formulae (P1) to (P4), $R^{511}$, $R^{512}$, $R^{513}$, $R^{521}$, $R^{522}$, $R^{523}$, $R^{531}$, $R^{532}$, and $R^{533}$ each independently represent a hydrogen atom or an alkyl group, m represents an integer of 0 to 2, and $R^{11}$ and $R^{12}$ each independently represent a hydrogen atom or a substituent, and in a case where m is 2, a plurality of $R^{11}$'s and $R^{12}$'s each may be different from one another.

14. The compound according to claim 12, wherein the ring $a^1$ and the ring $a^2$ have a nitrogen atom as a ring skeleton atom.

15. The compound according to claim 12, wherein the compound represented by General Formula (1) is a compound represented by General Formula (3):

General Formula (3)

[Chemical structure showing two fused quinoline rings connected, with substituents $R^1$, $R^2$, $R^3$, $R^4$, $R^5$ on one ring and $R^{101}$, $R^{102}$, $R^{103}$, $R^{104}$, $R^{105}$ on the other, with $O-A^1$ and $A^2-O$ groups]

in General Formula (3), $A^1$ and $A^2$ each independently represent a substituent containing at least one crosslinkable group selected from the group consisting of a vinyl group, an epoxy group, and a (meth)acryloyl group, and $R^1$ to $R^5$ and $R^{101}$ to $R^{105}$ each independently represent a hydrogen atom, a halogen atom, a hydrocarbon group having 1 to 10 carbon atoms, or an alkoxy group having 1 to 10 carbon atoms.

16. The compound according to claim 12, wherein $A^1$ and $A^2$ are each independently a group represented by General Formula (4):

General Formula (4)

—(Alkylene-O)$_{n2}$—C(=O)—C(R$^{531}$)=C(R$^{532}$)(R$^{533}$)

in General Formula (4), Alkylene represents an alkylene group having 2 to 6 carbon atoms, $R^{531}$, $R^{532}$ and $R^{533}$ each independently represent a hydrogen atom or an alkyl group, and n2 represents an integer of 0 to 10, and in a case where n2 is 2 or more, a plurality of Alkylene's may be different from one another.

17. The compound according to claim 15, wherein $A^1$ and $A^2$ are each independently a group represented by General Formula (4):

General Formula (4)

—(Alkylene-O)$_{n2}$—C(=O)—C(R$^{531}$)=C(R$^{532}$)(R$^{533}$)

in General Formula (4), Alkylene represents an alkylene group having 2 to 6 carbon atoms, $R^{531}$, $R^{532}$ and $R^{533}$ each independently represent a hydrogen atom or an alkyl group, and n2 represents an integer of 0 to 10, and in a case where n2 is 2 or more, a plurality of Alkylene's may be different from one another.

18. The curable composition according to claim 7, comprising the (meth)acrylate monomer having one (meth)acryloyl group in the molecule.

* * * * *